＃US005673691A

United States Patent [19]

Abrams et al.

[11] Patent Number: 5,673,691
[45] Date of Patent: Oct. 7, 1997

[54] APPARATUS TO CONTROL DIET AND WEIGHT USING HUMAN BEHAVIOR MODIFICATION TECHNIQUES

[75] Inventors: Philip S. Abrams, McLean; Al Behar; Orna Behar, both of Reston; Scott A. Brenneman, Falls Church; Lee W. Frederiksen, McLean, all of Va.; Nicholas C. Ide, College Park, Md.; Albert Jerome, Herndon, Va.; Donald A. Link, Columbia, Md.; Dennis J. Linnell, McLean, Va.; Marilyn J. Pritchard, Rockville; Hyam Singer, Silver Spring, both of Md.; Gerald J. Swisher, McLean, Va.; Catherine T. Timmerman, Silver Spring, Md.

[73] Assignee: PICS, Inc., Reston, Va.

[21] Appl. No.: 582,031

[22] Filed: Jan. 2, 1996

Related U.S. Application Data

[63] Continuation of Ser. No. 639,425, Jan. 11, 1991, abandoned.

[51] Int. Cl.$^6$ ............................ G06F 15/00; G09B 19/00
[52] U.S. Cl. ........................ 128/630; 128/921; 434/238; 434/247
[58] Field of Search ................. 364/709.03, 401 M, 364/413.29, 413.01, 413.02; 434/247, 238; 128/921, 630

[56] References Cited

U.S. PATENT DOCUMENTS

| | | | |
|---|---|---|---|
| 3,967,690 | 7/1976 | Northcutt | 177/25 |
| 3,991,304 | 11/1976 | Hillsman | 235/151.34 |
| 4,095,274 | 6/1978 | Gordon | 364/715 |
| 4,100,401 | 7/1978 | Tutt et al. | 235/92 T |
| 4,101,071 | 7/1978 | Brejnik et al. | 235/92 MT |
| 4,101,962 | 7/1978 | Hakata | 364/413 |
| 4,113,039 | 9/1978 | Ozaki et al. | 177/25 |
| 4,138,722 | 2/1979 | Bonnett | 364/415 |
| 4,159,416 | 6/1979 | Brejnik et al. | 235/92 MT |
| 4,192,000 | 3/1980 | Lipsey | 364/415 |
| 4,212,079 | 7/1980 | Segar et al. | 364/900 |
| 4,220,992 | 9/1980 | Blood et al. | 364/410 |
| 4,244,020 | 1/1981 | Ratcliff | 364/413 |
| 4,318,447 | 3/1982 | Northcutt | 177/25 |
| 4,321,674 | 3/1982 | Krames et al. | 364/413 |
| 4,366,873 | 1/1983 | Levy et al. | 177/25 |
| 4,380,802 | 4/1983 | Segar et al. | 364/900 |

(List continued on next page.)

FOREIGN PATENT DOCUMENTS 0033570  2/1984  Japan ........................ 364/413.29

OTHER PUBLICATIONS

"Nutri–Byte Analyzer: Your Personal Calorie and Nutrition Center"; *Journal of Nutrition Education*; v17 n4; 1985.

"Ambulatory Computer–Assisted Therapy for Obesity: A New Frontier for Behavior Therapy," Kent Burnett et al, *Journal of Consulting and Clinical Psychology*, 1985, vol. 53, No. 5, 698–703.

Newspaper article entitled "Computer Programs Range From Calorie Counters to Fitness Coaches," Washington Post Health, Aug. 14, 1985.

(List continued on next page.)

*Primary Examiner*—Gail O. Hayes
*Assistant Examiner*—Stephen R. Tkacs
*Attorney, Agent, or Firm*—Nixon & Vanderhye P.C.

[57] ABSTRACT

In the preferred embodiment, a hand-held computer prepares and monitors a goal-oriented weight, nutrition and exercise control program. Visual and audio prompts tell users when to eat and exercise, and provide suggestions for what to eat. The computer assists the user in setting safe goals for desired weight loss and the time required to achieve the loss. The user follows menu and exercise programs suggested by the computer. The computer records and analyzes the user's food consumption, exercise and weight loss programs. Finally, the computer displays feedback information regarding the user's progress towards achieving the desired weight.

38 Claims, 27 Drawing Sheets

U.S. PATENT DOCUMENTS

| | | | |
|---|---|---|---|
| 4,382,280 | 5/1983 | Mandel et al. | 364/412 |
| 4,423,792 | 1/1984 | Gowan | 177/25 |
| 4,464,121 | 8/1984 | Perelli | 434/236 |
| 4,464,122 | 8/1984 | Fuller et al. | 434/262 |
| 4,566,461 | 1/1986 | Lubell et al. | 128/668 |
| 4,571,682 | 2/1986 | Silverman et al. | 364/413 |
| 4,575,804 | 3/1986 | Ratcliff | 364/715 |
| 4,577,710 | 3/1986 | Ruzumna | 177/245 |
| 4,620,555 | 11/1986 | Schwarz | 131/270 |
| 4,629,015 | 12/1986 | Fried et al. | 177/25 |
| 4,683,891 | 8/1987 | Cornellier et al. | 128/630 |
| 4,686,624 | 8/1987 | Blum et al. | 364/415 |
| 4,709,331 | 11/1987 | Barkett et al. | 364/413 |
| 4,731,726 | 3/1988 | Allen, III | 364/416 |
| 4,775,935 | 10/1988 | Yourick | 364/401 |
| 4,796,182 | 1/1989 | Duboff | 364/413.29 |
| 4,807,169 | 2/1989 | Overbeck | 364/715.01 |
| 4,815,020 | 3/1989 | Cormier | 364/709.11 |
| 4,839,806 | 6/1989 | Goldfischer et al. | 364/413.02 |
| 4,853,854 | 8/1989 | Behar et al. | 364/413.01 |
| 4,855,942 | 8/1989 | Bianco | 364/561 |
| 4,855,945 | 8/1989 | Sakai | 364/709.02 |
| 4,891,756 | 1/1990 | Williams, III | 364/413.29 |
| 4,951,197 | 8/1990 | Mellinger | 364/413.02 |
| 4,954,954 | 9/1990 | Madsen et al. | 364/413.29 |
| 5,019,974 | 5/1991 | Beckers | 364/413.02 |

OTHER PUBLICATIONS

Food and Nutrition Information Center, *Microcomputer Software Collection*, A Bioliography, Feb., 1990, FNIC Software List, pp. 1–37.

"Nutrition for a Lifetime System: An Experimental Evaluation of a Prototype, Public Access Information System for Supermarkets," Winett et al, VIP and State University, Blacksburg, Virginia.

"Computer–Assisted Management of Weight, Diet, and Exercise in the Treatment of Type II Diabetes," Burnett et al, The Diabetes Educator, vol. 13, 1987 Special Issue, pp. 234–236.

"Developing Computer–Assisted Therapy for the Treatment of Obesity," Agras et al, Behavior Therapy 21, 99–109, 1990.

"Behavior Monitoring with Feedback Intervention," Burnett et al, Clinical Evaluation and Physioological Monitoring in the Home and Work Environment, pp. 1–10.

"Computers for Assessment and Intervention in Psychiatry and Psychology," Burnett, Dept. of Counseling Psychology, University of Wisconsin–Madison, Current Opinion in Psychiatry 1989, 2:780–786.

N–Squared Computing Analytic Software brochure.

"Nutri–Byte Analyzer: Your personal calorie and nutrition center," *Journal of Nutrition Education*, vol. 17, No. 4.

Nutri–Byte Analyzer brochure.

Nutri–Byte brochure.

Dietvalue product description, Dialog Accession No. 00011869, product released 1990, Practorcare, Inc. San Diego, CA.

Nutri–Calc for the Apple II 5.4 product description, Dialog Accession No. 01014785, product released Jul. 1987, CAMDE Corp, Tempe, AZ.

Nutri–Calc Plus 1.1 product description, Dialog Accession No. 01014783, product released Nov. 1986, CAMDE Corp., Tempe, AZ.

Mydiet product description Dialog Accession No. 0030878, product released 01 Jan. 1985, Software Toolworks, Chatsworth, CA.

Washington Post, Health section, 30 Jan. 1985, Squires, "Improving Diet, Byte by Byte", p. 14.

Patent Abstracts of Japan, vol. 12, No. 210, Abstract No. 63–8965, Kutsuwada et al.

Nutri–Calc product description, Dialog Accession No. 01014786, product released Jan 1988, CAMDE Corp, Temp, AZ.

Trim–Tech Professional product description, Dialog Accession No. 0033518, product released 01 Jul. 1989, DELTA GROUP, Aurora, IL.

Data Sources, 1989, Computer Associates Int., Garden City, NJ, pp. J–353 to J–355.

| 2004 BEHAVIOR HISTORY | 2002 CURRENT BEHAVIOR | |
| --- | --- | --- |
| | GOOD | BAD |
| CONSISTENTLY GOOD | MC1-2006 (POSITIVE-CONTINUOUS) "CONTINUE GOOD WORK" | MC2 (SLIP) "SNACKING CAN HAMPER YOUR PROGRESS" |
| INTERMITTENTLY GOOD | MC3 (INTERMITTENT-POSITIVE) "KEEP IT UP. EAT BREAKFAST TOMORROW" | MC4 (INTERMITTENT-NEGATIVE) "YOU SHOULD TRY TO EXERCISE NEXT TIME" |
| CONSISTENTLY BAD | MC5 (POSITIVE-NEW) "GOOD WORK! TRY TO DO IT AGAIN" | MC6-2006 (NEGATIVE-CONTINUOUS) "EATING TOO MUCH KEEPS YOU FROM YOUR GOAL" |

2000
FEEDBACK MATRIX

*Fig. 9*

```
═Choose Next Action══════════
    Breakfast
    Lunch
    Dinner
    Water
    Exercise today
    Weigh
    Bulletin Board            ▼
```

*Fig. 17*

```
═Select Menu════════════════
    Home
    Restaurant
    Planned Meal
```

*Fig. 18*

```
═Select Menu════════════════
    Quick & Easy
    From the Cookbook
    Frozen Foods
```

*Fig. 19*

```
═Choose Your Breakfast═══════
    Bagel Melt
    Bran Muffin & Fruit
    Canadian Bacon & Eggs
    Cinnamon Oatmeal & Banana
    Corn Flakes & Milk
    Egg on an English Muffin
    Lox & Bagels              ▼
```

*Fig. 20*

```
==Cinnamon Oatmeal & Banana===
  1¼ cup Hot oatmeal w/cinnamon
  1 med Banana
  8   oz Skim milk
```

Fig. 21

```
==Cinnamon Oatmeal & Banana===
  1¼ cup Hot oatmeal w/cinnamon
  1 med Banana
  8   oz Skim milk
                    ┌─────────────────┐
                    │ 373 calories    │
                    │  6% from fat    │
                    └─────────────────┘
```

Fig. 22

```
==Select Next Action===========
   Record this meal
   Substitute a food
   Change a quantity
   Request more information
```

Fig. 23

```
==Select a Substitute==========^
   1 med Nectarine
   2 med Peach
   1 med Pear
   6   oz Pineapple juice
   2 med Plum
   4   oz Prune juice
   1 wdg Watermelon
```

Fig. 24

```
==Cinnamon Oatmeal & Banana==
  1¼ cup Hot oatmeal w/cinnamon
  1   wdg Watermelon
  8   oz  Skim milk
```

*Fig. 25*

```
==Cinnamon Oatmeal & Banana==
  1¼ cup Hot oatmeal w/cinnamon
  1   wdg Watermelon
  8   oz  Skim milk
                   ┌─────────────────┐
                   │ 360 calories    │
                   │  6% from fat    │
                   └─────────────────┘
```

*Fig. 26*

```
==Enter Your Name==
Please enter your first name or
nickname, one letter at a time.

Jeff_
↑ and ↓       Changes each item.
Go On         Moves highlight right
Go Back       Moves highlight left.
```

*Fig. 27*

```
==Indicate Your Sex==
   Woman
   Man
```

*Fig. 28*

```
==Give Your Birth Date==========

Jul   5,  1951

↑ and ↓    Changes each item.
  Go On      Move highlight right.
  Go Back    Move highlight left.
```

Fig. 29

```
==Record Your Height===========
Your height is used to determine
your weight range.  Please
adjust the numbers below to show
your height without shoes.

5 feet     9 inches
```

Fig. 30

```
==Record Your Weight===========
The weight you give is your
starting point in the program.
Please provide your current
morning weight without clothes.

170.0 pounds
```

Fig. 31

```
==Select Your Activity Level===
Average activity
  Job involves heavy labor
  Bedridden
```

Fig. 32

=Check Your Personal Data=
Jeff, you are a male
born on Jul 5, 1951. You weigh
170.0 lb. and are 5' 9" tall.
You are active.

Is everything correct?

Fig. 33

=Set Weight Goal=
Change the weight shown below to
your desired long-term goal.

My weight goal is 150 pounds.

Fig. 34

=Set Short-Term Goal=
Your short-term goal is to lose
9 pounds in the next 6 to 8
weeks.

Plan a reward for yourself when
you reach it!

Fig. 35

=Set Short-Term Goal=
Your short-term goal is to lose
9 pounds in the next 6 to 8
weeks.

Pl Is this short-term goal OK?
yo

Fig. 36

```
=Confirm Your Mealtimes=======
              Weekday    Weekend
Breakfast     7:00 am    7:30 am
Lunch        12:00 pm    1:00 pm
Dinner        6:00 pm    8:00 pm ┌─────────────────────────┐
    │ Are these times correct?│
    └─────────────────────────┘
```

Fig. 37

```
=Choose Your Program==========
Three meals with no snacks
Three meals with one snack
```

Fig. 38

```
=Choose Your Exercises=====^
√Aerobics - fast
 Aqua-Aerobics
 Badminton
 Basketball
 Boxing - sparring
 Calisthenics
√Cycling - slow           ▼
```

Fig. 39

```
=Change Quantity==============

8  oz Skim milk
```

Fig. 40

```
==Change Quantity==
    6  oz Skim milk
```

*Fig. 41*

```
==Select Exercise==
Aerobics - fast       7 min.
Cycling - slow       11 min.
Other
```

*Fig. 42*

```
==Select Exercise==
A                          in.
C| Be sure to ease into any |in.
O| new exercise to protect
 | yourself from injury or
 | sore muscles.
```

*Fig. 43*

```
==Record Exercise Time==

Aerobics - fast

How long did you exercise?

27 minutes
```

*Fig. 44*

```
=Exercise Results=========
In 27 minutes of
Aerobics - fast
you burned 281 calories!
```

Fig. 45

```
Nice job.  Making exercise a
habit is great for your looks
and health.
```

Fig. 46

```
=Today's Summary==========
                   Target    Actual
Total Calories      1600       951
%Calories from fat    30        22
Number of meals        3         2
Number of snacks       0         0

Exercise calories     65       281
```

Fig. 47

```
=Good Afternoon, Jeff=====
- Just say no to snacks!
- Stick to foods low in fat.
- Eat enough, while avoiding
  high-fat foods.
```

Fig. 48

```
==Enter Calories===========
This option allows you to record
this meal using calories. Enter
the total calories eaten below.

640 calories
```

Fig. 49

```
==Meal Planning============
  Create or modify your plan
  Create an automatic plan
  View a planned meal
  Planning or viewing completed
```

Fig. 50

```
==Select Day to Plan=======
  Thursday   Dec 20    B L
  Friday     Dec 21
  Saturday   Dec 22
  Sunday     Dec 23
  Monday     Dec 24
  Tuesday    Dec 25
  Wednesday  Dec 26        ▼
```

Fig. 51

```
==Select Meal to Plan - 12/20==
  Breakfast
  Lunch
  Dinner
  Snack
  Stop
```

Fig. 52

```
=Select Dinner for 12/20=====
  Home
  Restaurant
```

Fig. 53

```
=Select Dinner for 12/20=====
  Quick & Easy
  From the Cookbook
  Frozen Foods
```

Fig. 54

```
=Select Dinner for 12/20=====
  Baked Orange Roughy w/Herbs
  Catfish Creole
  Chicken Marsala
  Chicken w/Fruit
  Chili w/Winter Squash
  Crispy Chicken
  Hobo Chicken                ▼
```

Fig. 55

```
=Dinner for 12/20============
  4  oz   Cranberry juice
  1       Crispy chicken breast*
  ¾  cup  Spaghetti squash
  ½  cup  Broccoli
  1  tsp  Soft margarine
  1       Baked apple*
```

Fig. 56

```
══Baking needs══════════════
   8  oz  All-purpose flour
   8  oz  Brown sugar
   2  oz  Sugar
```

*Fig. 61*

```
══Baking needs══════════════
√  8  oz  All-purpose flour
√  8  oz  Brown sugar
   2  oz  Sugar
```

*Fig. 62*

```
══Breads════════════════════
   1       Bagel
   6       Bran muffin
   6       Corn tortilla
   5  slc  Cracked wheat bread
   3  sm   Dinner roll
   3  slc  Italian bread
   3  sm   Multi-grain roll    ▼
```

*Fig. 63*

```
══Canned foods══════════════
   6  oz  Artichoke hearts
   2  oz  Lowcal fruit jam
  32  oz  Sliced peaches
```

*Fig. 64*

```
=Fish==========================
 14      Sea scallops
 12   oz Shrimp (peeled)
  2   oz Smoked salmon
  9   oz Swordfish
```

5,673,691

APPARATUS TO CONTROL DIET AND WEIGHT USING HUMAN BEHAVIOR MODIFICATION TECHNIQUES

This is a continuation of application Ser. No. 07/639,425, filed Jan. 11, 1991, now abandoned.

FIELD OF INVENTION

This invention is generally directed to a micro-computer apparatus and method for human behavior modification and control. The currently preferred embodiment employs an interactive goal-oriented program especially suited for helping an individual control his weight. The invention can be suited to modify other behaviors, as will be appreciated.

RELATED APPLICATIONS

The subject application is related to the following commonly assigned copending patent applications (each of which are hereby incorporated by reference and were filed on the same date):

Ser. No. 07/631,899, filed Jan. 11, 1991, entitled "A Timer For Protecting A Storage Battery In A Microprocessor Device," invented by Scott Brenneman et al (Atty. Ref. 247–55);

Ser. No. 07/639,424, filed Jan. 11, 1991, entitled "A Simplified User Interface for a Computer," invented by Philip Abrams et al (Atty. Ref. 247–61);

Ser. No. 07/640,108, filed Jan. 11, 1991, entitled "Hinge And Stand For Hand-Held Computer Unit," invented by Christopher Loew et al (Atty. Ref. 247–56);

Design Patent Application Ser. No. 07/640,010, filed Jan. 11, 1991, entitled "Hand-Held Computer Housing With Cover," invented by Christopher Loew (Atty. Ref. 247–58);

Design Patent Application Ser. No. 07/639,991, filed Jan. 11, 1991, entitled "Housing for a Hand-Held Computer," invented by Christopher Loew (Atty. Ref. 247–59), and Design Patent Application Ser. No. 07/639,993, filed Jan. 11, 1991, entitled "Hand-Held Computer," invented by Christopher Loew (Atty. Ref. No. 247–60).

BACKGROUND OF THE INVENTION

There are many weight control programs and devices. These programs vary from the fad and crash diets to structured nutritional programs that employ trained health professionals to set up individual weight-loss programs and monitor the individual's progress. Similarly, weight loss devices vary from appetite suppression diet pills to computer programs that set up nutritional diets.

Each of these programs and devices has shortcomings. The fad diets tend to, at best, offer short-term weight loss. Structured nutritional programs offer healthy diets, weight goals and encouragement to achieve long-term weight loss, if the individual is willing to regularly attend a diet clinic or hospital program. Many of the clinics require the purchase of specialty foods. Diet pills, like crash diets, provide short-term weight loss without any assurance of a healthy diet. Computer programs are useful in selecting nutritional diets and counting food calories, but are cumbersome to use and do not provide the goals and encouragement provided by a diet clinic or hospital program.

Counting the consumption of food calories is a common function of many weight control devices and programs. Existing electronic devices count food calories and perform additional functions. For example, U.S. Pat. No. 4,891,756 entitled "Nutritional Microcomputer and Method" issued to Williams in 1990, discloses a microcomputer which aids in the selection of foods, displays menus and nutritional information, and maintains a record of the nutritional values and calories of the foods consumed. Williams discloses an electronic nutritional reference that is akin to a reference book on nutrition.

Similarly, U.S. Pat. No. 4,321,674 entitled "Nutritional Value Accumulating And Display Device" issued to Krames et al. in 1982, discloses a microprocessor device for displaying nutritional values and accumulating these values for foods eaten each day. The Krames device calculates the total nutritional and caloric values for the foods anticipated to be eaten each day. These total values are compared to caloric limits entered into the computer and selected by the user. Krames discloses an enhanced calorie counter. Krames does not disclose a device for automatically establishing a dietary goal-oriented program to achieve a desired weight, or providing prompts at mealtimes or feedback about the dieter's progress.

There are several computer software programs that assist dieters in planning and following a weight control diet. For example, a promotional brochure for the "Nutri-Byte(TM) Analyzer" software states that the program provides nutritional and weight control assistance using a behavior modification approach. According to the brochure, the Nutri-Byte program "correlates hunger levels, moods, exercise, location, activity and company with eating behavior." The program purportedly assists the user in identifying those situations that prompt the user to eat. Apparently, the program can point out if the user eats in response to stress, anger or other situations. Presumably, once the user is aware of the situations that provoke eating, the user will know to avoid or not eat because of those situations. It appears that Nutri-Byte is a "behavior awareness program", rather than the managed diet and exercise program of the present invention that encourages healthy behaviors and helps the user to establish weight control habits. The Nutri-Byte program does not establish and monitor a weight control program.

An example of a device for modifying human behavior is disclosed in commonly assigned U.S. Pat. No. 4,853,854 entitled "Human Behavior Modification Which Establishes And Generates A User Adaptive Withdrawal Schedule" and issued to Albert Behar et al. in 1989. The Behar patent discloses a microprocessor device that applies behavior modification techniques to overcome habitual or addictive behaviors such as smoking. This device is programmable to create an individualized withdrawal schedule for the smoker and incorporates dietary strictures to aid the withdrawal program. This device has been found to be very effective to stop habitual behaviors such as smoking. However, the object of a weight control program is not to stop eating but rather to train the user to eat and exercise sensibly.

Similarly, U.S. Pat. No. 4,571,682, entitled "System And Method For Skill Enhancement And Behavior Modification" issued to Silverman et al. in 1986 discloses a group of computers that employ behavior modification techniques to improve sport skills. The Silverman computer monitors several physiological parameters of the athlete, analyzes these parameters to measure the athlete's performance, compares the actual performance to a desired performance and displays the athlete's actual performance and how it differs from the desired skill level. The athlete can adjust his performance to reduce this difference and improve his skill. Silverman does not disclose any weight control program. Since weight control has few similarities to learning sports skills, skill enhancement devices, such as disclosed in Silverman, are not suitable for weight control.

A portable diet software program is described in a research study entitled "Ambulatory Computer-Assisted Therapy For Obesity: A New Frontier For Behavior Therapy" conducted by Kent Burnett el al. and reported in the *Journal of Consulting and Clinical Psychology*, Vol. 53, No. 5 (1985) and in "Developing Computer-Assisted Therapy for the Treatment of Obesity," conducted by Agras et al. and reported in *Behavior Therapy*, Vol. 21, pp. 99–109 (1990). The Burnett study involved a computer program that records a dieter's food consumption and exercise activity, counts calories consumed as a percentage of daily caloric limit, and displays the available remaining calories for the day.

The Burnett software program was loaded in a portable laptop computer that the research subjects carried with them each day. In addition to recording food consumption and exercise activity and calculating caloric consumption, and the software program issued encouraging messages to the dieters regarding their diet and exercise progress. The computer program described in the Burnett study does not appear to have automatically established weight goals for the users, prompted the users when to eat and exercise, offered suggestions regarding diet selection, provided weekly reports regarding weight loss progress or monitored weight. Rather, the Burnett program seems to have been limited to monitoring caloric intake and expenditure, and providing feedback to the user. By controlling the caloric intake of the user, the user of the Burnett program lost weight.

SUMMARY OF THE INVENTION

Prior to the present invention, there was no portable weight control device and method that applied behavior modification techniques to establish weight goals for a dieter; prompt the dieter when and what to eat, and when and how long to exercise; provide feedback regarding the dieter's progress on a daily and weekly basis, and track the dieter's weight loss over a succession of months. There has been a long-term need for such a device and method.

The present invention, in its preferred embodiment, is a hand-held micro-computer weight control device that generates visual and audio prompts to signify times to eat, drink water and exercise, and prescribes what to eat and in what quantities and duration of exercise. The device also assists the user in setting safe goals regarding the individual's desired weight loss and the rate at which to achieve the desired weight loss based on personal information provided by the individual. The user follows meal and exercise programs suggested by the device, and ues the device to record his food consumption, exercise activity, and weight loss progress. Finally, the device displays feedback information to the user to encourage, motivate, and support the user towards achieving the desired weight. Feedback is provided immediately upon recording food consumption, water and exercise, at the end of each day and weekly. Additionally, prompts are provided each morning reminding the user of areas to focus on. The computer tracks and displays on demand the history of the weight loss efforts. This hand-held computer provides a complete weight control program that is effective in achieving the desired weight and maintaining it, simple to use and portable.

The method of the present invention is a weight control program implemented in a hand-held microcomputer. The program combines recent research findings in the areas of nutrition science, behavioral psychology, and exercise physiology for a comprehensive, scientifically sound approach to weight control. The present inventive method is based on the best available scientific knowledge about weight loss and weight control, combined with the benefits of advanced computer technology. The program offers a healthy and effective approach to weight loss.

There are two areas of behavior that most affect weight loss and long-term weight control. These are eating patterns and exercise habits. Reduce caloric intake with proper nutrition and moderate exercise are the cornerstones of the method of the present invention.

Proper nutrition involves eating balanced, healthy meals of readily available foods that provide the range of nutrients for good health. More than 200 menus, modified to meet an individual user's needs at five different caloric levels, are incorporated in the preferred embodiment of the present invention. The menus were developed in consultation with nutritionists to ensure that the program meets USDA and USDHHS Dietary Guidelines for Americans (USDA, USDHHS 1990). As such, the menus are based on commonly eaten foods and follow the recommendations for numbers of servings from each of the major food groups. The menus also follow the guidelines of the National Research Council's Committee on Diet and Health recommendations regarding cholesterol, fiber, and decreased protein and increased carbohydrates (NRC, 1989a). The menus were also developed with guidelines that were based on the NRC's latest edition of Recommended Dietary Allowances (NRC, 1989b).

Changing exercise habits involves making a permanent lifestyle change to include regular exercise. The present invention provides a safe, flexible exercise program tailored to the abilities and needs of a wide range of users. The program follows the basic guidelines for exercise outlined by the American College of Sports Medicine (ACSM) (ACSM, 1986, 1990). The program prescribes exercise involving large muscle groups, practiced at moderate intensity 3 to 5 times per week for 20 to 60 minutes. The preferred embodiment of the inventive program prompts users to exercise 3 times per week and provides exercise duration targets based on the user's current levels of activity. The exercise protocol begins with minimal target exercise minutes and gradually shapes users to increase their exercise, while always remaining within the guidelines set by ACSM.

Research on behavior modification as applied to weight loss suggests that changing eating and exercise behaviors requires structure, clearly defined targets, and consistent monitoring and feedback. Therefore, the preferred embodiment of the present invention incorporates behavior modification procedures such as stimulus control, prompting, shaping, goal setting, and feedback. Stimulus control and prompting are used to encourage regular habits of eating three meals per day at consistent times and exercising three times per week. For example, an icon on the computer screen lights up, a tone sounds, and a written prompt appears to signal the individual when it is time to eat. In the exercise protocol the user is "shaped" to greater levels of exercise by providing gradually increasing targets for caloric expenditure per exercise session.

Goal setting, both short-term and long-term, is initiated by allowing individuals to set their own weight loss targets. Users select a long-term target weight and the computer generates a short-term weight loss goal that can be reached in six to eight weeks. The user can adjust the rate of which they prefer to lose weight by adjusting their short-term goal within a range determined to be safe by the invention. Finally, performance-based feedback is provided by the computer immediately following behaviors, at the end of the day, each morning, and at the end of each week. Feedback is geared toward increasing program compliance and is sensitive to the history of behavior. For example, the first occurrence of a behavior is treated differently from an ongoing pattern.

The net effect of these changes in eating and exercise behaviors is steady, gradual weight loss. Dramatic and rapid weight loss is known to be unhealthy and short-lived, and leads to metabolic changes that may make future weight loss increasingly difficult. In the preferred embodiment, the present invention adjusts caloric levels on the basis of changes in weight until the rate of weight loss is optimized in the range of 1–2 lbs. per week, depending on the weight of the individual.

Appropriate adjustments and warnings are provided should the user be found to be losing weight too rapidly or not making progress.

Because the invention is a computerized program, precision, flexibility and immediacy in weight monitoring and caloric adjustment can be achieved where they are not possible with traditional programs. As a result, the present invention can automatically provide a program tailored specifically to each user that monitors and adjusts dynamically for changes in weight and behavior during program use.

After users reach their desired weight, the preferred embodiment of the program provides for weight maintenance automatically. During maintenance, daily caloric levels are adjusted to stabilize weight, and the program continues to reinforce those eating and exercise behaviors that led to weight loss and that can now be used for weight control. Should the user be unable to maintain his goal weight, the invention will automatically recommend that he set a new goal. Alternatively, the preferred embodiment can be used strictly to maintain an existing weight and, thus, is not restricted to weight loss. Furthermore, the invention in another contemplated embodiment can set up and monitor dietary programs to reduce cholesterol levels, and to control diabetes, stress, hypertension and other health conditions.

One of the inventive program's unique aspects is that it is "personalized" for each individual. The computer tailors each weight-loss program to the user's sex, age, height, weight, weight loss goals, exercise preferences, and usual mealtimes. In addition, the program monitors caloric intake at each meal and adjusts subsequent meals during the day to account for overeating or under eating. Caloric and exercise targets are adjusted weekly on the basis of user compliance with the program and multi-week trends in weight. A user's weight control program is personalized in order to provide an optimal program.

Another aspect of the personalization of the present invention is that it caters to individual lifestyles by including a wide range of menu types. For example, menus of foods that are quick and easy to prepare can be displayed by the computer. Conversely, the computer can display menus that are more elaborate when more preparation time is available. A selection of commercially available frozen foods is included to round out the at-home menus. In addition, a host of restaurant menus can be included in the computer memory to provide choices ranging from fast food to a variety of ethnic cuisines. When chosen with reasonable variety, the meals prescribed by the invention adhere to the nutritional guidelines discussed above.

Likewise, the exercise protocol caters to diverse lifestyles by including a wide range of activities such as walking, swimming, cycling, aerobics, and tennis. The individualized exercise prescriptions are based on a user's baseline level of exercise and degree of adherence to the program and are adjusted as required.

The invention has additional features which offer both convenience to the user as well as support of weight-loss behavior. They include the ability to plan meals, create shopping lists and view graphs of progress.

The hand-held computer of the present invention is designed to be simple to use—especially by those with no previous experience with computers. In a preferred embodiment, the computer has only nine buttons and operation involves simply moving a highlighted cursor from place to place on the screen to indicate choices and the use of "Yes" and "No" buttons to answer questions. The screen includes both a text area as well as a set of graphic symbols that are used in prompting behavior. The computer has an extensive on-line help system that can be invoked by the press of a single "Help" button. The help system is designed to provide immediate assistance for the most likely problems that users might be experiencing at any given point in the program.

The hand-held weight control device of the preferred embodiment is a computerized self-management program that is highly interactive. It is meant to be carried throughout the day to assist the user with important behaviors such as selecting when and what to eat, when and how much to exercise, and when to drink water. The device is both proactive and responsive to user actions. It initiates actions through a real-time prompting system, cueing users when to engage in various behaviors. Users, in turn, respond by recording what they do; and the device responds further by providing various types of feedback and adjusting caloric intake prescriptions and exercise targets dynamically in response to user behaviors and changes in weight.

The interactive real-time processing that characterizes the hand-held device of the preferred embodiment makes it unique among behavior change and management methodologies. The weight control device achieves a level and degree of interaction and immediate responsiveness to user actions and changes in weight that are not possible with traditional clinic-based or therapist-guided treatments, nor with self-management programs delivered via traditional formats, e.g., printed material, audio cassettes, or videocassettes.

The purpose of the weight control computer is to allow users to establish a structured, consistent routine for enhancing compliance with diet programs and for achieving long-term weight change and maintenance. The weight control computer establishes specific goals for a wide range of individual behaviors, prompts users to engage in certain behaviors at appropriate times, provides feedback regarding the user's performance, and alters the program based on the user's compliance and success.

BRIEF DESCRIPTION OF THE DRAWINGS

FIG. 9 is a chart showing the matrix of categories for feedback messages;

FIGS. 17 through 66 is a series of exemplary screen displays showing the operation of the preferred embodiment.

DETAILED DESCRIPTION OF THE DRAWINGS

Figure 1:
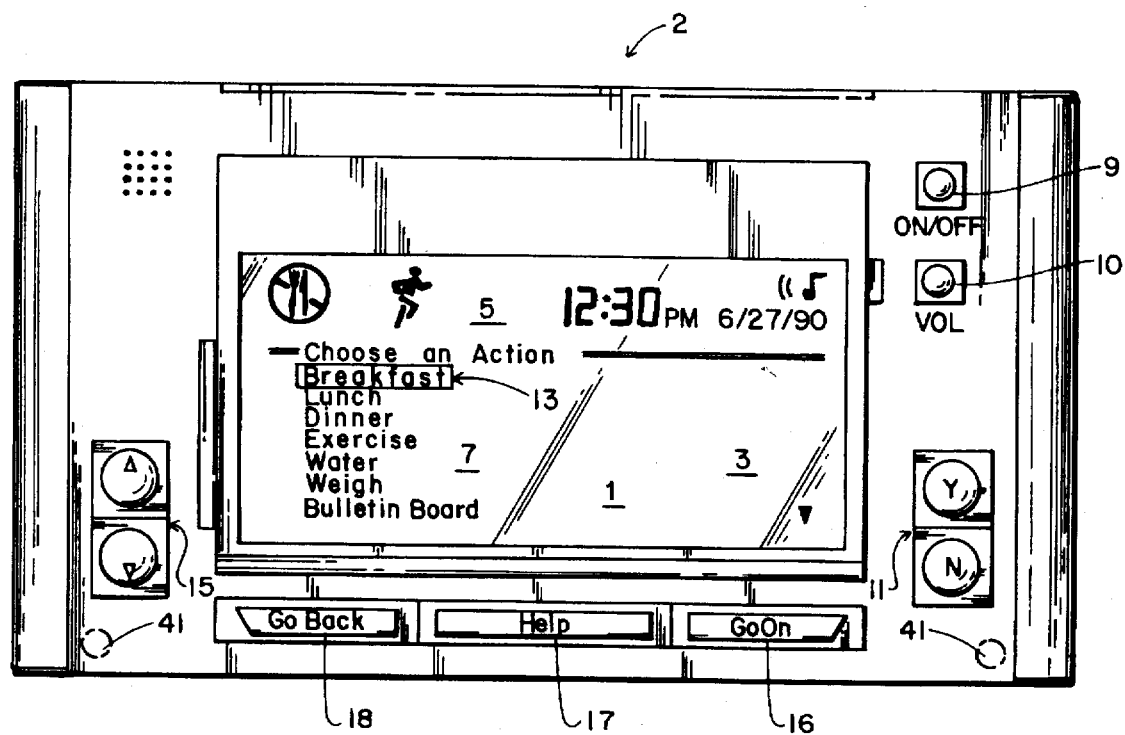
FIG. 1 is a plan view showing the display and controls of the hand-held computer in the preferred embodiment of the present invention.

FIG. 1 shows the face 1 of the hand-held weight control computer 2 of the preferred embodiment. There is a display 3 and a series of buttons on the face of the computer. The display is large enough to be read easily by a user. The computer is small enough so as be a hand-held device. It fits easily into a large purse or into a suit breast pocket. The buttons on the face of the computer are arranged to be easily reached by the thumbs and other fingers of the user when the computer is held in a user's hands.

Surrounding the display are nine control buttons. These include the on/off button 9 that turns the computer on and off, a volume button 10 that adjusts the volume of the audio prompts and responses, a button pair 11 that provide for yes and no responses by the user, a button pair 15 that move the cursor bar 13 up or down in the display, a Go On button 16 that completes a transaction and causes the display to show a following informational screen, a Go Back button 18 that terminates a transaction and causes the display to show the preceding informational screen, and a help button 17 that produces a display of instructional text to assist in using the computer. Since there are only nine buttons, the computer is extremely user friendly even to the most inexperienced computer user.

Figure 2:
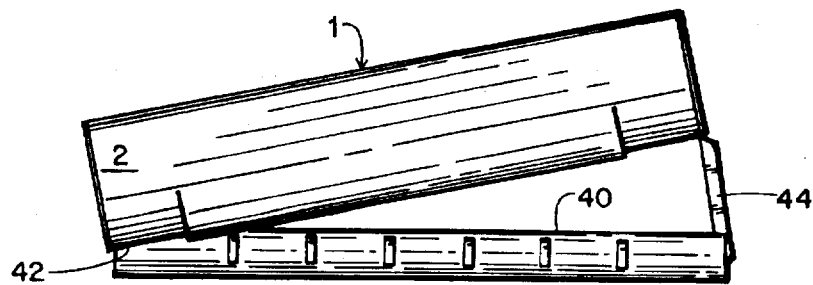
FIG. 2 is a side view of the hand-held computer shown in FIG. 1 in which the lid is shown as being folded over for use as a base for the computer.

As seen from FIG. 2, the weight control computer is slim and compact. There is a lid 40 that covers the display face 1 in a closed position. Magnets 41 on the face of the computer hold the lid closed by being attracted to metal pads (not shown) on the inner surface of the lid. When open, the lid folds underneath the computer and slides into a lip 42 in the bottom of the computer. The lid and hinge in the open position form a base for the computer that tilts the display face towards the user when the computer is placed on a flat surface, such as a table. A folding plastic hinge 44 secures the lid to the computer. This hinge is described in detail in the related application Ser. No. 07/640,108 entitled "Hinge And Stand for Hand-Held Computer Unit" and incorporated by reference above.

As shown in FIG. 1, the display 3 comprises a liquid crystal screen that is segregated into a prompt area 5, and a text and graphics area 7. There are four icons that can be displayed in the prompt area, in the preferred embodiment. These icons prompt the user to eat or not, drink water, exercise and weigh himself. The icons are shown on the display when the user is to perform the activity represented by the icon. For example, an icon of a runner becomes visible when it is time to exercise. The icons remain visible until the user records the activity into the computer or until the preferred period of time for the activity elapses. In the case of eating, a two and one-half hour period is set within which to eat each meal. Thus, the eating icon is displayed for two and one-half hours or until the user eats in response to the icon. When it is not time to eat, a "don't eat" icon appears in place of eat icon. The prompt area 5 also includes a display of the time and date.

In addition to the icons, the computer provides other prompts to the user. Appropriate activities are also prompted by an audio alarm and a textual display, such as "Breakfast time now!" By following the prompts, the user develops a structured routine of eating meals at consistent times, exercising three times per week, weighing daily, and drinking water at regular intervals throughout the day.

The text and graphics area 7 of the display is used to present the user with various selections, e.g., types of restaurants and menus; encouraging messages, e.g., "It's good to eat breakfast"; feedback regarding progress, e.g., "You have lost 6 lbs. in three weeks"; and graphics charts of progress. The text area of the screen is used to prompt the user to enter personalization information and to record meals, exercises and weights. Indeed, the text area, combined with the icons, is the principal communication channel from the device to the user.

I. Electronic Components of Unit

Figure 3:
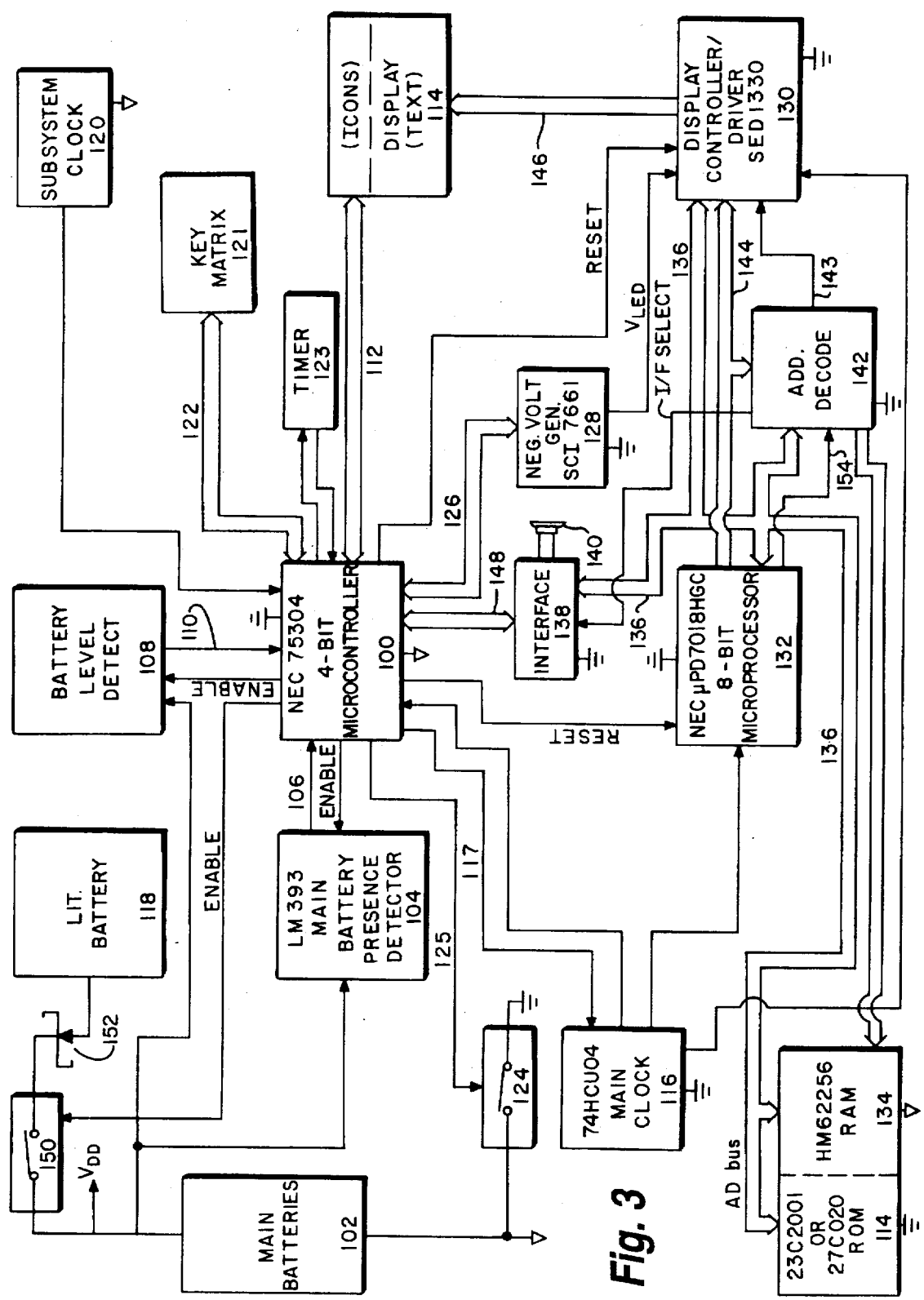
FIG. 3 is a simplified block diagram of the microprocessors and other electronic components that comprise the hand-held computer shown in FIG. 1.

FIG. 3 is a block diagram of the computer and display in the weight loss computer. There are two microcomputers that control the unit. A four-bit microcontroller 100, which in the preferred embodiment is an NEC μPD75304, is always active and monitors and controls most of the other electronic components. The microcontroller uses its own internal program and data storage areas that provide it with 4 k bytes of ROM and 512 bytes of RAM.

The 4-bit microcontroller monitors the battery power for the computer. A set of main batteries 102 provides power for the computer through $V_{dd}$ connections to various other components. All of the block components shown in FIG. 3 receive voltage $V_{dd}$ with the exception of the key matrix 121, the display 114, the subsystem clock 120, and the lithium battery 118. A main battery presence detector 104 signals the 4-bit microcontroller over line 106 that a set of batteries is in the main battery compartment. This presence detector indirectly senses that the main batteries are physically in the battery compartment by initially sensing the voltage level $V_{dd}$. The detector's threshold is approximately 3.5 $V_{DC}$, below which it is inferred that the main batteries are absent. Until the presence detector signals the existence of main batteries, the computer will not operate except in a lithium battery mode described later. During operation, the voltage level of the battery is detected by the battery level detector 108 that sends a signal to the 4-bit microcontroller representative of the voltage level of the main batteries.

The 4-bit microcontroller scans the keys of the key matrix 121 over bus 122. When the power-on key is depressed, the 4-bit controller closes the switch 124 to ground to cause power to be provided to all components. Before closing this switch, the 4-bit controller enables the main battery presence detector 104 to ensure that batteries 102 are installed and enables the battery level detector 108 to ensure that the voltage is sufficiently high to allow operation.

A watch-dog timer 123 regularly confirms that the 4-bit microcontroller is operating properly. The watch-dog timer is a pulse generator that must be periodically cleared or it will reset the controller. The microcontroller is programmed to repeatedly clear the timer. If the microcontroller does not clear the timer within a prescribed time, then the watch-dog timer will reset the microcontroller. Generally, the microcontroller will operate properly after being reset.

The 4-bit controller also adjusts the contrast in the display 114. Messages regarding the contrast are sent over bus 126 to a negative voltage generator 128. In response to this message, the negative voltage generator sets the voltage level of $V_{lcd}$ that is fed to the display controller 130. The display controller sets the contrast level in the display as will be discussed below. There are sixteen contrast levels that can be selected by the user.

The 4-bit microcontroller controls an 8-bit microprocessor 132 that is either a NEC μPD70108HGC or an OKI MSM80C88A, in the preferred embodiment. The 8-bit processor has an associated address latch that is not shown. A main clock generator 116 provides pulsed signals to the microcontroller 100, processor 132 and the display controller 130 so that the processor and controllers can communicate with each other. In the preferred embodiment, the 8-bit processor receives a clock pulse train of 3.2768 MHz, the 4-bit controller receives a pulse train at one-half of that rate (1.6384 MHz), and the display controller receives a quarter rate clock pulse at 819.2 KHz.

The 8-bit processor runs the programs that interact with the user. For example, the 8-bit processor runs the program that allows the user to enter personal information that is used by the computer to tailor a weight control program to that individual. Other programs, discussed below, present menus on the display, establish goals for the user, record a user's food consumption and exercise, provide informative feedback messages on the user's behavior, prepare progress reports and charts for the user and a variety of other functions.

The programs for the 8-bit processor are embedded in ROM 160, which, in the preferred embodiment, has 2M bits of capacity arranged as 256K bytes. The personalization information entered by the user and the meals, weight and exercise information recorded by the user are stored in the RAM 134. The RAM has a 256K bit capacity arranged as 32K bytes. The processor accesses these memories via a combined address and data bus 136. The program and data storage areas for the 4-bit microcontroller are internal to that device.

There is an interface latch 138 that couples the 4-bit microcontroller to the bus 136. In the preferred embodiment, the latch is a 74HC174 latch. The interface unit allows data transfer between the 4-bit controller and the 8-bit processor. There is a 2-bit bus 148 between the 4-bit controller and the interface unit. This data transfer is accomplished by a command/response protocol that uses serial data transfers controlled by handshake lines. The 8-bit processor initiates any data transfer over bus 148 and thus serves as a master processor to the 4-bit controller for data transfer. The 8-bit processor, via the interface unit, also operates a piezo-electric speaker 140 that emits tones and plays tunes when the user is to eat or perform other behaviors as well as responding to user inputs.

An address decode logic unit 142 decodes the addresses put on the bus 136 by the 8-bit processor. In the preferred embodiment the address decoder comprises a standard set of components, such as 74HC04, 74HC10, 74HC74, 2N3904. Depending on the address, the address decoder issues select signals to the ROM or RAM, the display controller, or the interface logic unit. An M/IO line 154 selects between memory and input/output addressing in the 8-bit processor's address map. In the I/O space of this address map is located the addresses for the interface for the 4-bit microcontroller and the display controller. To select the display controller, the address decoder enables the display select line 143. To select the microcontroller the processor enables latch 138 via the I/F select line 137. In addition, there is a separate RAM enable signal operated by the 4-bit controller that protects RAM data. This RAM enable signal allows or disallows the RAM to receive the chip select signal from the address decoder. When the RAM is disallowed from recieving chip select signals, e.g., by the on/off switch activating switch 125, the RAM will no act on any extraneous pulse signals generated by the address decoder.

If the display controller 130 is selected, then display information is read from or written to the display controller by the 8-bit processor over bus 136. The control lines 144 for the read and write functions convey read RD and write WR signals from the processor to the address decoder and the display controller. The display controller, in turn, controls the text area of the display 114 through a standard dot matrix driver program. Text to be presented on the display is provided by the 8-bit processor to the display via the display controller. The display controller is coupled to bus 136 that allows for data transfers between the display controller and the 8-bit processor.

When the user is between key strokes and the 8-bit processor is not needed, the 8-bit processor instructs the 4-bit microcontroller to maintain the 8-bit processor in a powered but halted mode with the main clock stopped. Similarly, the 8-bit processor instructs the microcontroller to turn off power to the processor when the user turns off the unit or after a few minutes of no events or activity on the key matrix (timeout). If a key is pressed or a preprogrammed event occures, e.g., a meal time, the 8-bit processor is revived when the 4-bit controller starts the clock for the processor and resets the 8-bit processor. The 4-bit controller conveys information, such as any pending events, and key presses, to the 8-bit processor via bus 148, interface 138 and bus 136.

If the 8-bit processor and display are on and processing of the most recent event is complete, then the 8-bit processor will set a wake-up timer in the 4-bit controller, request that the controller issue a clock freeze signal, and go into a halt mode. The 4-bit controller then sends a freeze signal over line 117 to the main clock to the 8-bit processor, but the main clock and the display controller continue to maintain the display.

When an event occurs or the wake-up timer goes off, the 4-bit controller verifies that sufficient voltage exists, unfreezes the main clock and resets the 8-bit processor. Assuming that there was no event and the wake-up time signaled, the 8-bit processor clears the display, does any housekeeping tasks that are needed, requests a power down, and goes into its halt mode again. If it is time for an event, the 8-bit processor will process the event that is to occur.

In time-out or power-down, the 4-bit controller removes power to all circuits except itself and some support circuitry. The 4-bit-controller runs off of the subsystem clock 120 and only updates its own timers and slowly scans the key matrix 121. The 4-bit controller turns the 8-bit processor back on only if a key is pressed, or a preprogrammed event (e.g., next meal) occurs.

If the user presses the ON/OFF switch to turn off the unit, the 8-bit processor power-down sequence is followed as described above, and the 4-bit controller turns off the icon section of the display, and itself goes into a halt mode. The user turns the unit back on by pressing the ON/OFF key again. The ON/OFF key is tied to the interrupt line of the 4-bit controller, which wakes up and then brings up the 8-bit processor in the fashion described above.

II. Software and Operation Overview

Figure 4:
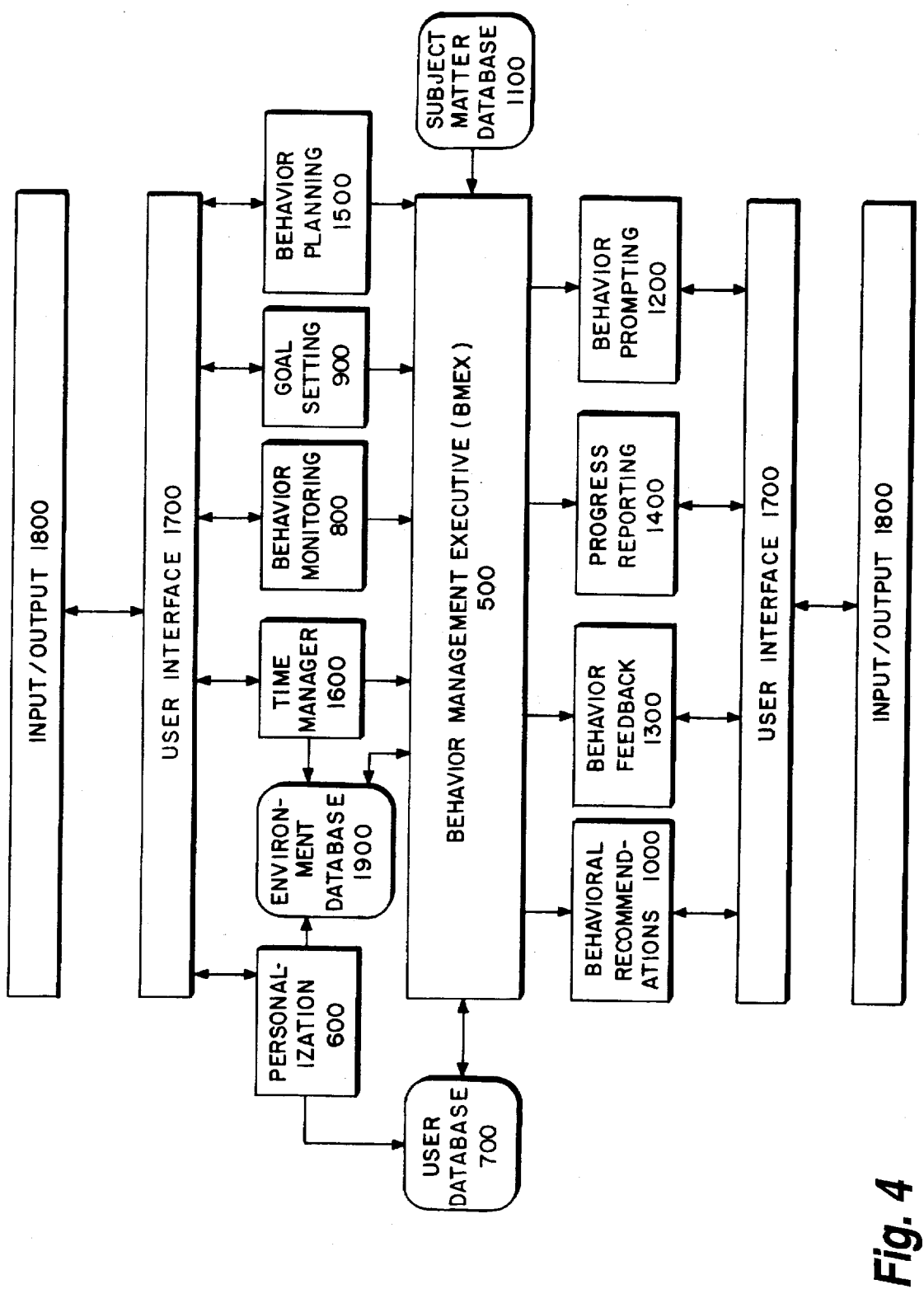
FIG. 4 is a general block diagram of the software routines that are executed by the hand-held computer shown in FIG. 1.

FIG. 4 shows a block diagram of the software routines that operate within the preferred embodiment of the weight control computer. In summary, a Behavioral Management Executive (BMEX) routine 500 interacts with users to help them achieve a particular behavioral goal or goals, such as weight and/or diet control. BMEX is a collection of several significant software routines used to implement the weight/exercise management program. The purpose of the BMEX is to assist the user both to lose and maintain weight and to develop new behaviors that will help him maintain a healthy weight long-term.

The BMEX receives information about the user's personal characteristics (e.g., sex, age, weight); behavior (e.g., eating habits, exercise habits), and desired weight goal (e.g., lose 20 pounds in 5 months, or maintain current weight within 5 pounds). In addition, a modified BMEX could be used to implement other goals for desired behavior such as to reduce risk of heart attack, control chronic headaches, to control food intake for persons with dietary restrictions such as diabetes, or persons suffering from heart disease or hypertension and/or improve a user's time management.

The BMEX receives the information on personal characteristics and desired goals in several ways. Information about the user is gathered through a Personalization routine 600 that prompts the user to key in information about age, sex, and other personal characteristics. It is contemplated that user information could be fed into the BMEX directly from an electronic scale, pedometer, a heartbeat counter, a blood testing instrument, a urine analyzer and many other medical instruments that monitor the human body. Personalization information is stored in a User Database 700 kept in RAM 134. Similarly, data regarding the overall environment (such as the time and date and user personal identification number) are stored in an Environment Database 1900 also kept in RAM 134.

Direct observation of user behavior is obtained from a Behavior Monitoring routine 800 through which the user regularly enters information regarding his behavior. The user is reminded when to perform the various behaviors by the Behavior Prompting routine 1200. During the first several weeks of the weight control program, the information entered through the behavior monitoring routine is used to form a baseline of the user's behavior. With the baseline, the BMEX tailors the behavior program to the user's habits, e.g., time and length of exercise, and preferences, e.g., favorite meals on certain days of the week. Behavior information recorded later in the program is used to monitor the extent to which the user adheres to the program and reaches his desired goals. The collected information is stored in the User Database 700. The User Database stores detailed behavioral information for the most recent 15-day period, e.g., specific menus chosen by the user, calories eaten, exercises performed. Weekly summary information, e.g, total calories eaten, weight, total exercise calories, are stored for two years in the User Database. These data are used for analysis and feedback to the user and can also be extracted for use in longer-term research.

Figure 5:
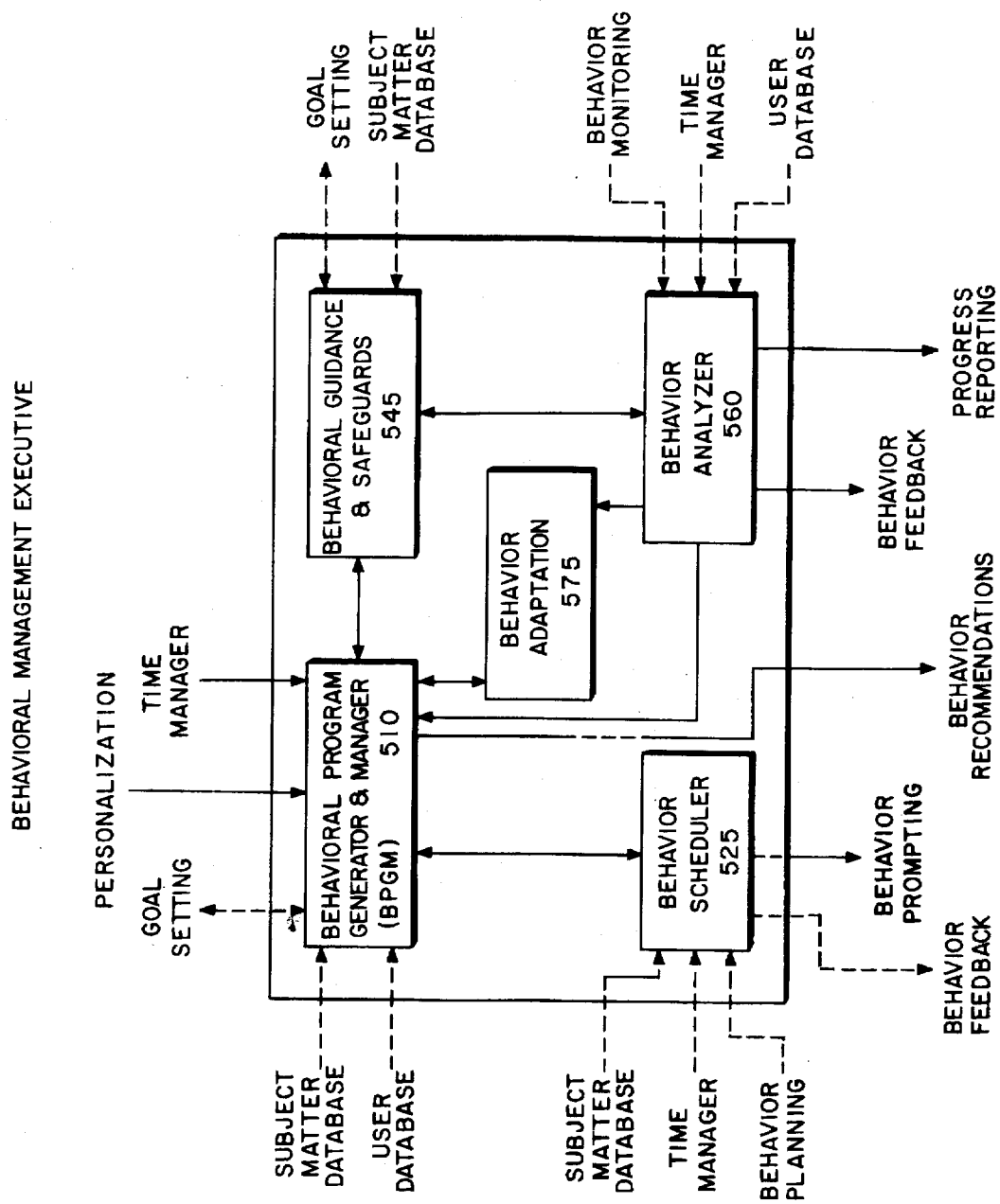
FIG. 5 is a more detailed block diagram of the Behavioral Management Executive software routine shown in FIG. 4.

Behavioral goals are established through a Goal Setting routine 900 that can either automatically set goals for the user or allow the user to interact with the computer to select his individualized goals. The goals can be revised by the user at any time. Based on the collected information, a personalized Behavior Management Program is developed by the Behavioral Program Generator and Manager (BPGM) routine 510 within the BMEX and shown in FIG. 5.

The personalized Behavior Management Program tells the user when to engage in various behaviors via the Behavior Scheduler routine 525. The scheduler prompts the user through icons, verbal messages, and audio signals at the proper times to eat, drink, exercise, and weigh himself. Other prompts could be used such as a vibration that could be given to the user to silently advise him to perform the desired behavior or synthesized speech could be used for the same purpose.

The BMEX routine 500, using the Behavioral Program Generator and Manager also recommends specific aspects of scheduled (and unscheduled) behavior via a Behavioral Recommendations routine 1000 which presents to the user recommended behaviors such as menus for meals to be eaten, and type and duration of exercise to be done. These recommendations are based on the behavioral goals and other data obtained from the User Database and a Subject Matter Database 1100 stored in ROM 160.

Recommendations made by the Behavioral Recommendation routine 1000 are checked by a Behavioral Guidance and Safeguards routine 545 prior to being proposed to the user. The recommendations are finally shown to the user by the Behavior Prompting routine 1200. The Behavior Prompting routine selects appropriate messages and/or an icon from the Subject Matter Database 1100 to be displayed to the user. There is an extensive library of messages stored in the Subject Matter Database. This library is indexed by categories that correspond to various activities and feedback reports. The Behavior Prompting routine is instructed as to what activity is to be prompted by the Behavior Scheduler routine and then looks up the appropriate category in the Subject Matter Database for that activity. Once the appropriate message category is selected, then a message within that category is chosen (randomly or otherwise) and displayed to the user. The random selection of messages ensures that the user is presented with slightly different messages for the same activity and, thus, guards against monotony while offering the appearance of intelligent behavior by the computer.

The user keys in his actual behavior by interacting with the Behavior Monitoring routine 800, which records the behavior in the User Database for historical analysis as well as input to the Behavior Analyzer 560. The recorded actual activity is compared to the recommended behavior by the Behavior Analyzer routine 560. When necessary, changes to the behavioral program are made by a Behavioral Adaptation routine 575 to account for the degree of user adherence and success at meeting behavioral goals and subgoals.

At appropriate times, the user receives positive or negative feedback concerning his behavior. The feedback text messages are displayed in the text area 7 of the display and the messages are generated by the Behavior Feedback routine 1300. Behavior feedback is originated by the Behavior Analyzer 560. The Behavior Analyzer provides regular feedback each morning and evening, immediately following recording of each behavior, and once a week. Morning feedback concentrates on those behavioral areas in which the user has been exhibiting problems or in which a change in behavior patterns is recognized. The morning feedback is presented as a series of short messages designed to provide guidance to the user during the coming day. Typical morning messages might be "Don't forget to eat breakfast," "Be sure to exercise today," or "Eat more low-fat foods today."

Morning feedback is prepared at the beginning of each day and is presented to the user as soon as the device is turned on or upon the user performing the first action of the day, if the device was left on all night. After being presented, morning messages are also stored in the User Database 700. At any time during the day, the user can request these messages again through Progress Reporting 1400. This is done by the user selecting the Bulletin Board option from the main menu. When presented subsequently through the Bulletin Board, the messages are modified in two significant ways. First, if a prescribed behavior has already been recorded via the Behavior Monitoring routine 800, the associated message is not repeated. In the example above, once the user eats breakfast, the Bulletin Board will no longer contain a reminder to eat breakfast. Second, as discussed above, the actual text of a message may vary because of the random selection from the appropriate category of messages. For example, the message regarding exercise might be repeated as "Exercising today is important!" in contrast to the first message of "Be sure to exercise today."

Evening feedback is treated similarly. Evening feedback is created at the end of each day, generally an hour after dinner. It is intended to provide a summary of the day's activities, with both positive and negative feedback. Evening feedback considers the day's activities in the context of the activities of the past two weeks. As with morning feedback, the evening summary focuses on problems or changing behaviors. Evening feedback messages are more extensive than morning messages as they review the day just completed and look to the future. When the evening messages are prepared, the prompt "Bulletin Board Ready" appears on the display accompanied by an audio cue. The user must select the Bulletin Board option to review evening feedback messages. The user may read the Bulletin Board, in which the evening messages replace the morning messages. The evening messages remain until the messages for the next morning are presented. The evening messages are modified dynamically in the same way as the morning feedback.

Weekly reviews are prepared every seven days. These are presented at the same time as each seventh day's evening messages. The weekly feedback is more analytic and reflective than daily feedback. It is designed to offer the user a periodic overview of his progress, and encouragement or caution in an interpretive context regarding the user's behavior. A typical weekly review might be:

This has been a good week for you.
You lost 1.5 pounds. Continue to follow the program closely every day.
You are doing a fine job!
You're right on track sticking close to your goal weight. Don't worry if you see some small changes. It's perfectly normal to fluctuate a few pounds above or below this weight. By following the meal plan more carefully and increasing your exercise, you'll be sure to maintain the great progress you have made.

In addition to verbal feedback about prior behavior, the Progress Reporting routine 1400 provides quantitative feedback about measurable information such as weight, calories eaten, and exercise calories expended. These data are presented both as tables and as graphs showing long-term trends.

Specific feedback on an individual action can be provided immediately after it is recorded by the user while he is interacting with the Behavior Monitoring routine 800. This instantaneous feedback provides the user with praise or suggestions for alternative behaviors. Examples of immediate feedback are: "You did well eating breakfast today. Keep it up tomorrow"; "You should try to exercise more next time," and "Snacking can hamper your progress." The combination of instantaneous, daily and weekly feedback are extremely effective in implementing a complete Behavior Modification Program.

There are several other routines that enhance the BPGM and support the BMEX. For example, achievement of the user's behavioral goals is aided in some situations by the user planning for future behavior (e.g., planning for future meals). Planning for future behavior is accomplished with the Behavior Planning routine 1500. For example, the user can plan his meal menus for two weeks and have the planning routine prepare a shopping list for all his planned meals. Similarly, sound guidance and safeguards are incorporated into the Behavioral Guidance and Safeguards routine 545 and applied to ensure that the program followed by the user is safe and healthy. For example, users trying to lose weight are cautioned against trying to lose weight too rapidly. The Behavioral Guidance and Safeguards routine accesses the Subject Matter Database 1100 to retrieve information regarding dietary guidelines, safe exercise limits, healthy maximum weight losses and other such information. In addition, a Time Manager routine 1600 provides information regarding the current time (date, time-of-day, day-of-week, elapsed time, and the user's concept of the beginning of a new day). The Time Manager supports many of the other routines that require knowledge of the current time. Finally, interaction with the user is managed by the User Interface routine 1700, which makes optimum use of the available Input/Output devices 1800, e.g., display screen and a nine button keyboard.

III. Software Routine

The BMEX uses the above-mentioned routines as required to help the user achieve his own behavioral goal or goals, as well as developing new behavior that will contribute to his ability to sustain desired results long-term. Many of these routines are well-known in the prior art. For example, there are many commercially available routines that set up databases for microprocessor controlled devices or generate messages regarding the date and time. Depending upon the microprocessor controller being used, a person of ordinary skill will be able to set up these routines with no more instruction than provided above. However, for the sake of completeness, further descriptions of many of the routines are given below.

a. Behavioral Program Generator and Manager

The Behavioral Program Generator and Manager (BPGM) 510 generates an initial Behavior Management Program based on user data and goals, as well as associated built-in behavioral goals. The BPGM also coordinates all other system routines as required to meet these goals. The main purpose of the BPGM is to help the user select healthy and attainable behavioral goals, and to achieve those goals in an appropriate time frame. The BPGM assists the user to develop new behaviors that will contribute to long-term maintenance of goals.

The BPGM begins a program by soliciting the user's input of his personal characteristics and needs, by calling Personalization 600. The BPGM then continues by helping the user establish appropriate goals (e.g., to lose 15 pounds in 10 weeks) by calling up the Goal Setting routine 900. The Goal Setting routine invokes the Behavioral Guidance and Safeguards routine 545 that indicates appropriate goals and rates of behavior change (e.g., medically sound goal weight range, and safe rates of weight loss). In addition to the user's goal or goals, the Goal Setting routine and the BPGM may each add several additional goals that are related to achieving the user's goals and maintaining the desired results long-term (e.g., eating 3 balanced meals each day, regular exercise, reducing snacking, keeping fat intake under 30% of total calories).

After the user's goals are established, the BPGM accesses the Subject Matter Database 1100 and the User Database 700 to determine appropriate behavioral recommendations to support goal achievement (e.g., the daily caloric consumption for the user to lose 1.5 pounds per week, and when the user should eat each meal of the day). In conjunction with the Behavior Scheduler 525 and the Behavioral Recommendations routine 1000, the BPGM presents to the user screens and audio prompts that tell him when to engage in certain behaviors (e.g., when to eat breakfast, when to exercise), and recommend specific aspects of those behaviors (e.g., meal choices at the appropriate caloric level, duration of exercise).

The BPGM adjusts its Behavior Management Program based on actual user behavior (e.g., when the user actually eats breakfast, what does he eat for lunch, and when and how long does he exercise). Information on actual user behavior is entered by the user while interacting with the Behavior Monitoring routine 800. The recorded data of actual behavior is processed by the Behavior Analyzer routine 560 that outputs information to the Behavioral Adaptation routine 570 that adjusts the Behavior Modification Program held in the BPGM. For example, if the user is not losing weight as expected at some particular caloric level, that level would be adjusted downward until the expected rate of weight loss is observed, while making sure not to go below the minimum healthy level of caloric intake.

In addition to program adjustments, the Behavior Analyzer provides screens of user feedback through the Behavior Feedback routine 1300. The feedback to the user is designed to influence the user's behavior to comply with the selected goals. For example, a user who consistently skips breakfast will be reminded that doing so is counter to success, and will be assertively reminded to eat breakfast at appropriate times.

Figure 6:
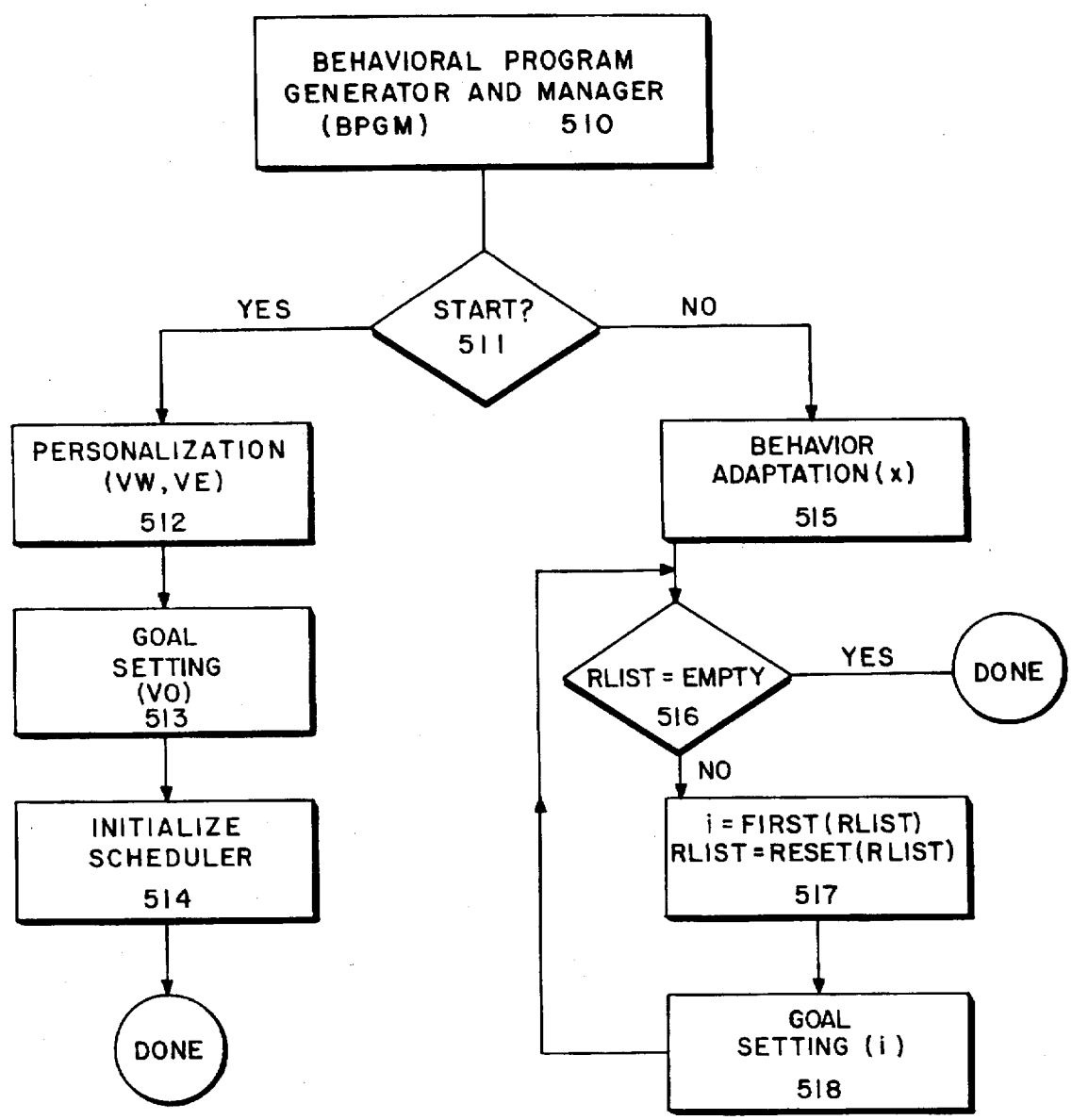
FIG. 6 is a flowchart for the Behavioral program Generator and Manager routine.

FIG. 6 is a flowchart of the Behavioral Program Generator and Manager 510. The BPGM functions both at the beginning of the program and throughout the duration of the program. In step 511, a test is made to determine whether the BPGM is beginning a program.

If it is the beginning, BPGM invokes Personalization 600 in step 512 which requests the user to provide values for critical personal data such as age, height, weight and sex. The list VW contains the indices (i) of those variables Vi stored in the User Database 600 that are to be personalized. The list VE contains the indices (j) of those variables Vj stored in the Environment Database 1900 to be initialized.

Step 513 calls the Goal Setting routine 900 with parameter VO. VO is the list of indices (j) of objective variables Vj for which goals are to be set. The goals for variables Vj are recorded in the User Database with index VGoal(j). VGoal(j) is a mapping function that defines the correspondence between a variable index (j) and the index of the variable containing the value of its goal.

Step 514 initializes all the events in the scheduler. Each event is characterized by parameters—

Type
(e.g., meal/exercise)
Start Time
End Time

The Behavior Scheduler 525 has the task of generating prompts based on the events in its event queue.

When not used for personalization or other initialization functions, the BPGM is activated by the Time Manager 1600 any time there has been a change in a behavioral variable or at the beginning of each day.

In step 515, the Behavior Adaptation routine 575 is invoked with argument 1. This signals the Behavior Adaptation routine that it was called from the BPGM. The effect of Behavior Adaptation is to review all behavior variables. If there is any problem encountered, Behavior Adaptation may adjust one or more variables. It may also require a change of a goal by the user. Variables to be changed are set in a list RList. On return from Behavior Adaptation, step 516 tests whether RList is empty. If so, there is no further work to be done. Otherwise, execution continues at step 517, which sets the variable (i) to be the first element of the list RList. RList is reset to contain all but the first element. In step 518, the Goal Setting routine 900 is called for the variable Vi. This might occur when, for instance, the user has entered his weight and it is the same as the goal weight. The Behavior Analyzer and Behavior Adaptation routines note that the user is at his weight goal by setting the index for the variable containing today's weight in the list RList. When the BPGM is next invoked, it will cause the Goal Setting routine to request a new goal weight from the user.

b. Behavioral Guidance and Safeguards Routine

The Behavioral Guidance and Safeguards routine (BGS) 545 is responsible for: 1) providing the user with informed guidance related to his Behavioral Goals (e.g., recommended ideal weight based on user's sex, age, height, etc.); 2) enforcing any safety restrictions on the user's Behavioral Goals (e.g., don't allow a weight goal that is too low, or a rate of weight loss that is too rapid); 3) ensuring that any Behavior Management Program generated by the BPGM 510 follows sound medical and safety considerations (e.g., recommended food intake consists of sufficient daily calorie levels), and 4) informing the user when his behavior is unsafe (e.g., he is eating too much fat, or not enough calories).

The BGS is primarily a collection of logic rules acting on information concerning medical and other safety considerations, stored in the Subject Matter Database 1100. The BGS interacts with the Goal Setting routine 900 when that routine establishes user behavioral goals. Similarly, the BGS obtains information on user behavior from the Behavior Analyzer routine 560, and then gives warnings and suggestions to the Behavior Analyzer to pass on to the user via the Behavior Feedback routine 1300.

Figure 7:
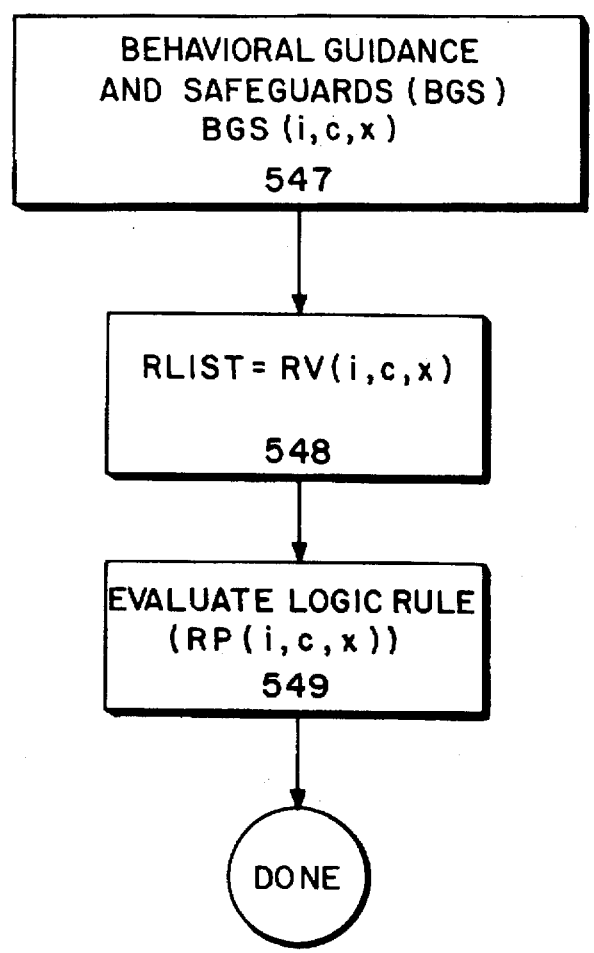
FIG. 7 is a flowchart for the Behavioral Guidance and Safeguards routine.

As shown in FIG. 7, the Behavioral Guidance and Safeguards routine 545 invokes a set of logic rules or predicates of the form RP(i,C,x). Each rule RP(i,C,x) is a rule for variable Vi in the User Database in the context C. This rule is used to evaluate whether the value for Vi is within acceptable limits. X is the proposed value for the variable Vi. Context C can be personalization, post-behavior, weekly, or another context. The context parameter allows the possibility of multiple logic rules for any single variable, based on the various contexts or circumstances in which the variable is applied.

A rule (predicate) RP(i,C,x) can take into account values in the Subject Matter Database 1100, the User Database 700 and the Environment Database 1700. A corresponding function RV(i,C,x) sets the range of acceptable values for each rule.

As an example, the rule RP(i,C,x) for an acceptable weight goal, as set in Personalization, has the form RP(wg, Pers,X) where wg is the index of weight goal variable WGOAL, and Pers is personalization. The rule RP(wg,Pers, X) is defined as follows:

```
define RV (wg,Pers,X)
    begin
        RList = lowwt(age,height)
        RList = RList, highwt(age,height)
    end
define RP(wg,Pers,X) = ((X ≥ RList[1]) and
    (X ≤ RList [2]))
```

In the above, the first two lines of the definition of RV set RList to be a two item array in which the first item is the result of the function lowwt, which determines the lowest safe weight for a given age and height. The second item in RList is highwt. The predicate RP returns the value of True if X is both greater than or equal to the lowest weight (lowwt) and less than or equal to the highest weight (highwt). The implementation of the lowwt and highwt functions, in the preferred embodiment, is as follows:

```
lowwt(age,height) = 2.2046*BMIL*(height/39.37)²
    where BMIL = (if age < 35 then 19 else 21)
highwt(age,height) = 2.2046*BMIH*(height/39.37)²
    where BMIH = (if age < 35 then 25 else 27)
```

These functions, lowwt and highwt, are based on recommendations stored in the Subject Matter Database.

c. Behavioral Adaptation Routine

The Behavioral Adaptation routine 575 is responsible for adjusting the Behavior Management Program based on actual versus recommended behavior. For example, if the user is not losing weight at the desired rate, the Behavioral Adaptation routine can suggest to the BPGM either to reduce the average daily caloric intake being used for recommended meals, or to increase the recommended level of exercise. In a stress reduction application, the Behavioral Adaptation routine might instruct the BPGM to increase the amount of daily stress reduction activities recommended to the user during a particularly stressful period. The Behavioral Adaptation routine also adjusts upcoming behavioral recommendations based on currently observed behavior (e.g., if the user eats a large lunch, then the recommended dinner will contain fewer calories than if the user had eaten a lunch at the recommended calorie level; or if the user exercises a lot one day, the recommended dinner for that evening could allocate some additional calories).

Figure 8:
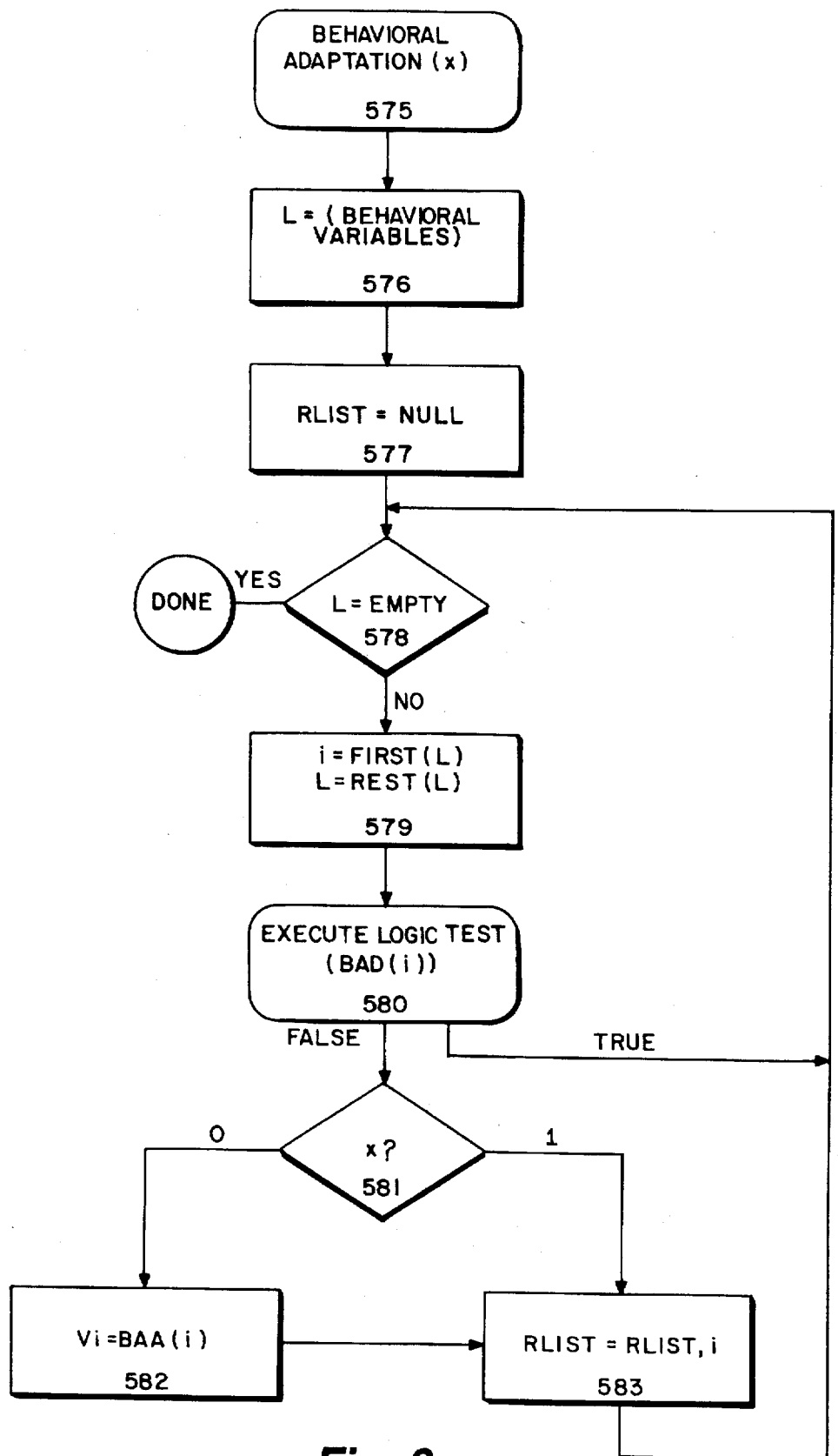
FIG. 8 is a flowchart for the Behavioral Adaptation routine.

FIG. 8 is the flowchart for the Behavioral Adaptation routine 575. The Behavioral Adaptation routine can be called either by the BPGM or by the Behavior Analyzer 560. In the former case, the BPGM solicits a set of variables for which goals are to be set. In the latter case, behavior adaptation makes the adjustments itself. The cases are differentiated by the value of the parameter X which is 1 if called by BPGM, 0 if called by the Behavior Analyzer.

In step 576, the variable L is set to be the list of all behavioral variables in the program. In the rest of the routine, each variable's value will be examined with respect to its goal and its history, and appropriate action taken. Step 577 sets RList to empty. RList will be used to accumulate the output of Behavioral Adaptation. Step 578 tests to see if L is empty, which occurs when all variables originally set into L have been examined. When L is empty, the routine is done. Otherwise, execution continues at step 579, in which the variable (i) is given the value of the first item of L, which is the index of the next variable to be examined. L is then reset to be all but the first item in L.

In step 580 the logic test BAD(i) analyzes the value of variable Vi. The analysis can be a function of any or all variables in the User Database, the Environment Database and the Subject Matter Database. A value of True means that the value of the variable Vi is appropriate and that no action need be taken. In this case, execution continues at 578 to look for the next variable.

If the result of the analysis is False execution continues at 581, where the value of the parameter X is examined. If it is 0, meaning that the Behavioral Adaptation routine was called by the Behavior Analyzer 560, then the routine continues to step 582. Otherwise, it goes to step 583. At step 582, function BAA(i) is called to compute the Behavioral Adaptation adjustment for variable Vi which is then set into variable Vi. At step 583, RList has appended to it the index of the variable under consideration.

As an example, consider the variable DTCAL which is the daily target of calories to be eaten. If dt is the index ("address") of DTCAL, then the definitions of BAD(dt) and BAA(dt) are as follows:

```
define BAD(dt)
begin
    EVAL  := if (no weight loss progress) then -3
             else if (weight loss too slow) then -1
             else if (weight loss rate unsafe) then 3
             else if (weight loss too fast) then 1
             else 0 (weight loss OK)
    if EVAL = 0 then return(TRUE) else return(FALSE)
end
define BAA(dt)
begin
    EVAL  := if (no weight loss progress) then -3
             else if (weight loss too slow) then -1
             else if (weight loss rate unsafe) then 3
             else if (weight loss too fast) then 1
             else 0 (weight loss OK)
    DTCAL := DTCAL + EVAL*100
    DTCAL := min(2400, max (LOW, DTCAL))
end
```

The Behavioral Adaptation routine obtains information on user behavior from the Behavior Analyzer 560 which in turn receives information from a variety of other routines.

d. Behavior Analyzer Routine

The Behavior Analyzer 560 tracks data over time (time information is obtained from the Time Manager 1600), builds a user history within the User Database 700, and performs various analyses on these data. The Behavior Analyzer provides support for the BPGM 510, Behavioral Adaptation routine 575, and the BGS 545 in evaluating user behavior, which is recorded by the Behavior Monitoring routine 800.

For example, in the preferred embodiment, the Behavior Analyzer: a) tracks user exercise and eating over the first few weeks of a weight reduction program in order to provide the BPGM 510 with a behavior baseline to utilize in its refinement of the Behavior Management Plan for the user; b) determines average daily caloric intake over a certain period of time to allow the BGS 545 to assess the soundness of the user's actual diet; c) tracks weekly weight to determine average weekly weight loss to allow the Behavioral Adaptation routine 575 to adjust the weight loss program as required to lose weight faster or slower; d) determines the user's daily meal choices so that the BPGM can recommend (via Behavioral Recommendations 1000) the favorite meals as the user's first choice for planning meals on the appropriate days.

The Behavior Analyzer also tracks and analyzes user behavior so that progress reports can be displayed to the Progress Reporting routine 1400. The Behavior Analyzer maintains data on how the user is doing in relation to his own behavioral goals and the generic goals established by the Goal Setting routine 900 and the BPGM 510. For example, the Behavior Analyzer maintains data that shows: a) weight loss over time in relation to the user's target weight; b) average daily fat consumption in relation to a general goal of less than 30% of total calories from fat; c) average minutes of exercise per week in relation to a weekly exercise goal.

The Behavior Analyzer is central to the creation of feedback messages, as discussed earlier. There are several unique aspects to the feedback provided. Feedback is given at different times to accomplish different purposes: in the morning, feedback reminds the user of important behaviors that day; in the evening, feedback reviews the day's performance; weekly, the feedback provides a goal-oriented overview of the week's progress; and following each behavior, feedback provides immediate positive or negative reinforcement of the action just registered.

Another aspect is that feedback is enhanced by having the computer tailor the feedback messages to the user's current behavior and his behavior history. For example, if the user has a recorded history of consistently not eating breakfast and then one morning he records that he ate breakfast, the feedback message might be "It's great that you ate breakfast—try to eat it again tomorrow." In contrast, if the user has eaten breakfast every morning for the past two weeks and did so today, then there may be no feedback message given because the habit of eating breakfast is well established and does not require constant reinforcing feedback. Thus, the messages are selected to be appropriate to the behavior and the user's history for that behavior.

In the preferred embodiment, the subject matter database has a variety of feedback message categories based on the feedback matrix 2000 shown in FIG. 9. The feedback matrix describes a way to characterize patterns of dichotomous behavior. The rows of the matrix are captioned "Current Behavior" 2002 and represent the immediate behavior recorded by the user. This immediate behavior can be "good" meaning that the prompted behavior was recorded as being performed or "bad" meaning that the behavior was not performed or not performed as recommended. Similarly, the columns of the matrix are captioned "Behavior History" 2004 and refer to the user's history in performing the same behavior as is the "Current Behavior." The history of the behavior is categorized as being consistently good, intermittently good, or bad. The six cells are named for their behavioral input. There is a separate feedback message class (MC#) 2006 for each of the six combinations in the matrix. Each message class corresponds to a group of similar messages in the Subject Matter Database that are appropriate for the current behavior in the context of the user's behavior history. FIG. 9 also shows a message example for each category.

Feedback in all these cases is based on the computer's ability to recognize the patterns of behavior and to respond accordingly.

Behaviors are characterized by three parameters (B,TF, BT) where:

B is the behavior itself (e.g., eating breakfast);

TF is the time frame (e.g., "morning", "post behavior", "weekly").

BT is the behavior type, a larger class which might include several behaviors (e.g., meals), and Feedback rules are based on all three of these parameters and have three components:

Criterion or trigger

Prior Behavior

Message Class

The criterion/trigger is the logical condition that is necessary to be satisfied in order to invoke the feedback message. It corresponds to the columns of FIG. 9. It is typically a function of the current behavior, possibly in the context of other relevant variables. The prior behavior is a logical condition based on history of the current behavior, possibly in the context of other relevant variables. If both the criterion and the prior behavior are true, then the system will produce a message chosen from a specified message class as was described above for FIG. 9.

Suppose for example that the behavior in question is daily weight entry. In this case, there is an array W of weight for the past 15 days with W[0] being today's weight, W[1] yesterday's weight, W[2] the day before yesterday, etc. If a weight is not entered for day i, the value of W[i] is 0.

The feedback rules for the daily weight entry behavior for evening feedback are as follows:

| Criterion | Prior Behavior | Message Class | Comment |
|---|---|---|---|
| W[0]>0 | PBB(W[ ]>0) | FM(1,w,p) | Positive-New (MC5) |
| W[0]>0 | PBI(W[ ]>0) | FM(2,w,p) | Positive-Intermittent (MC3) |
| W[0]>0 | PBG(W[ ]>0) | FM(3,w,p) | Positive-Continuous (MC1) |
| W[0]=0 | PBG(W[ ]>0) | FM(4,w,p) | Negative-Slip (MC2) |
| W[0]=0 | PBI(W[ ]>0) | FM(5,w,p) | Negative-Intermittent (MC4) |
| W[0]=0 | PBB(W[ ]>0) | FM(6,w,p) | Negative-Continuous (MC6) |

The predicates PBB( ), PBI( ) and PBG( ) used above are as follows:

```
define PBB(X)
    begin
        comment Prior Behavior Bad
        return((X[1]=0) and (X[2]=0) and
            (X[3]=0))
    end
define PBI(X)
    begin
        comment Prior Behavior Intermittent
        s := 0
        for i=1 to 3 do
            s := s+(if X[i]>0 then 1 else 0)
        return (if (s>0) and (s<3) then
            TRUE else FALSE)
    end
define PBG(X)
    begin
        comment Prior Behavior Good
        return((X[1]>0) and (X[2]>0) and
            (X[3]>0))
    end
```

Finally, to complete this example, the message classes are defined to contain messages as follows: FM(1,w,p)

Entering your weight today was an important step.

It was good that you weighed yourself today. Keep it up.

Recording your weight today got your program back on track.

Make a point of weighing in again tomorrow.

Good job weighing in today. It's an important part of the program. FM(2,w,p)

Keep up the routine of weighing yourself every day.

You're getting back into a good routine of weighing yourself.

You're developing a good habit of weighing in regularly.

Continuing to weigh in is important.

You're weighing in regularly. It's best to do so every day. FM(3,w,p)

You're consistently entering your weight. Great job.

It's great that you weigh yourself every day.

You're doing a fine job entering your weight consistently.

Your practice of weighing every day is good. Keep it up!

Your habit of weighing in every day helps DietMate to help you. FM(4,w,p)

You forgot to enter your weight today.

Be sure to weigh in tomorrow.

Don't skip weighing yourself. You'll do better if DietMate knows your daily progress.

Try to weigh yourself every day.

Weigh yourself every day. It's a good indicator of your progress. FM(5,w,p)

Don't get into a habit of skipping your daily weigh-in.

You forgot to record your weight this morning.

Don't make it a habit.

Even on busy mornings, don't forget to enter your weight.

Your scale missed you this morning. FM(6,W,p)

Alert ! It is critical that you enter your weight. The program cannot work without it!

Figure 10:
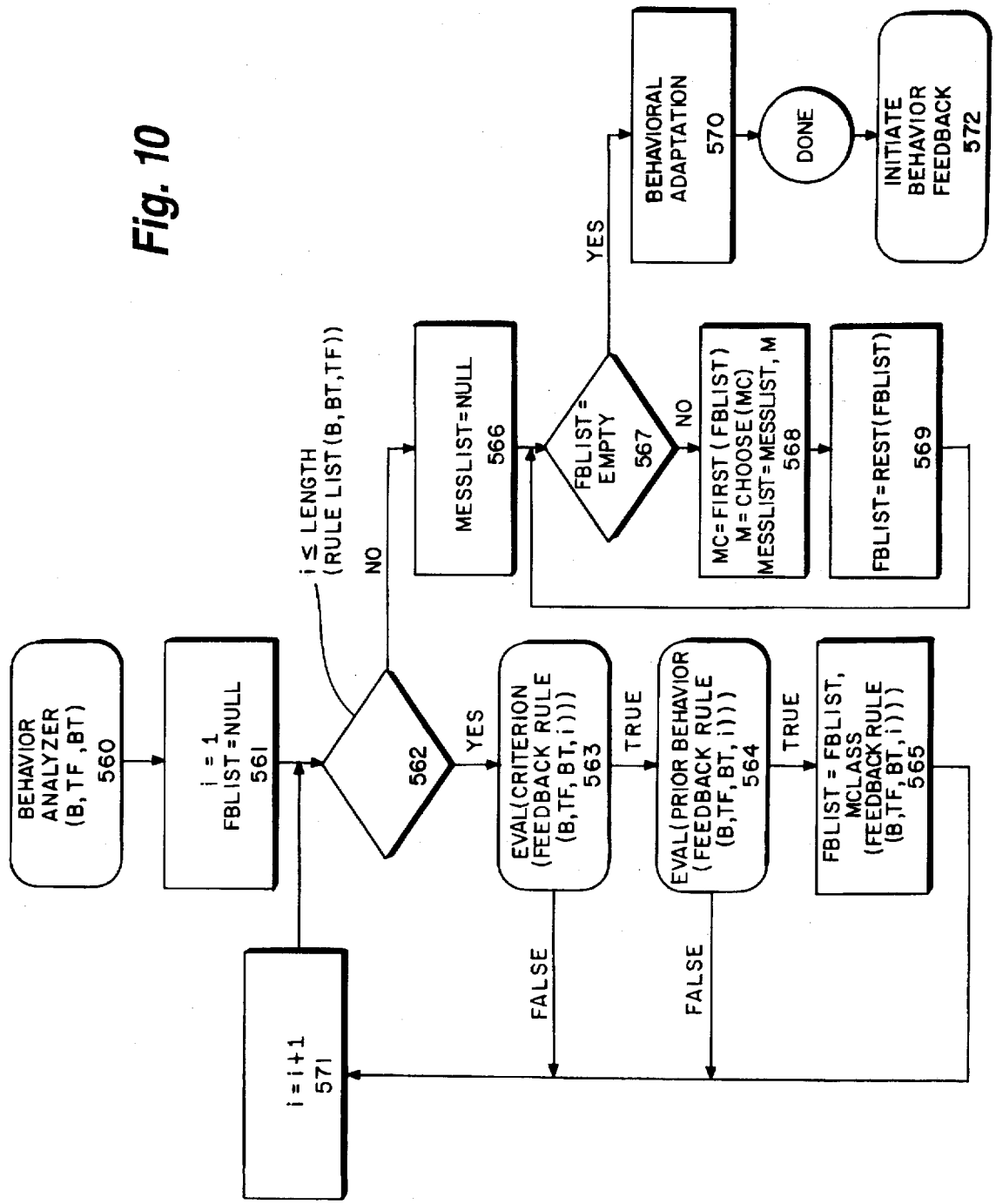
FIG. 10 is a flowchart for the Behavior Analyzer routine.

The flowchart in FIG. 10 describes the Behavior Analyzer 560.

Step 561 initializes variable (i) to 1. The variable (i) will be used to step through the set of all rules for the behavior B of type BT in time frame TF. Also, the list FBLIST of message classes for feedback messages is set to empty or null. At step 562 the value of (i) is checked against the number (length) of rules for the current behavior B, type BT and time frame TF. If all rules are exhausted, execution resumes at step 566. Otherwise, execution proceeds to step 563.

In step 563 the criterion part of the ith feedback rule for B, BT, TF is evaluated. If it is false, no further action is taken for this rule and execution goes to step 571. If the criterion is true, then step 564 evaluates the prior behavior part of the ith feedback for B, BT, TF. If it is false, then no further action is taken for this feedback rule and execution continues at 571. Otherwise, both the criterion and the prior behavior are true and execution moves to 565.

At step 565, the message class (MClass) of the ith feedback rule is appended to the list FBLIST. Execution goes to step 571, where the variable (i) is increased by 1 to process the next rule, if any.

The purpose of the loop from steps 566 through 569 is to choose messages from each message class in FBLIST to be presented to the user. Step 566 initializes the list MESSLIST to be NULL. Step 567 tests whether the test FBLIST created in the first part of behavior analyzer is exhausted. If so, the Behavior Adaptation is called at 570 to check for any variables that may need to be changed. Finally, the system initiates Behavior Feedback routine 1300 and Behavior Analyzer is done.

At step 568, the variable MC is set to the first item in FBLIST. The function Choose (MC) generates a message from the class MC. Choose can use any number of algorithms. For instance, it can be random or it can be based on history of messages already delivered. The message generated by Choose is appended to the list MESSLIST. In step 569, the first item is dropped from the list FBLIST and execution returns to step 567.

e. Behavior Scheduler Routine

The Behavior Scheduler routine 525 decides when to prompt the user for desired behavior (e.g., when to eat breakfast, when to exercise, when to weigh himself. The Behavior Scheduler receives inputs from the BPGM, the Time Manager 1600, and the Behavior Planning routine 1500. The Behavior Scheduler schedules behavior for specific dates, specific days of the week, or specific times of day, based on the user's particular schedule. The Behavior Scheduler also effectively schedules behavior far in advance to allow the user to make plans based on recommended future behavior (e.g., meal planning and shopping lists)—which is coordinated with the Behavior Planning routine 1500.

The Behavior Scheduler provides data to the Behavior Prompting routine 1200 which in turn reminds and/or actively prompts the user to engage in scheduled behavior. The Behavior Scheduler also provides information to the Behavior Feedback routine 1300 which gives the user feedback on his behavior. Feedback is in two forms: scheduled and unscheduled. Scheduled feedback occurs at certain times of day, such as first thing in the morning or at the end of day. Unscheduled feedback occurs in connection with a particular behavior, and is triggered when the user records his behavior.

Figure 11:
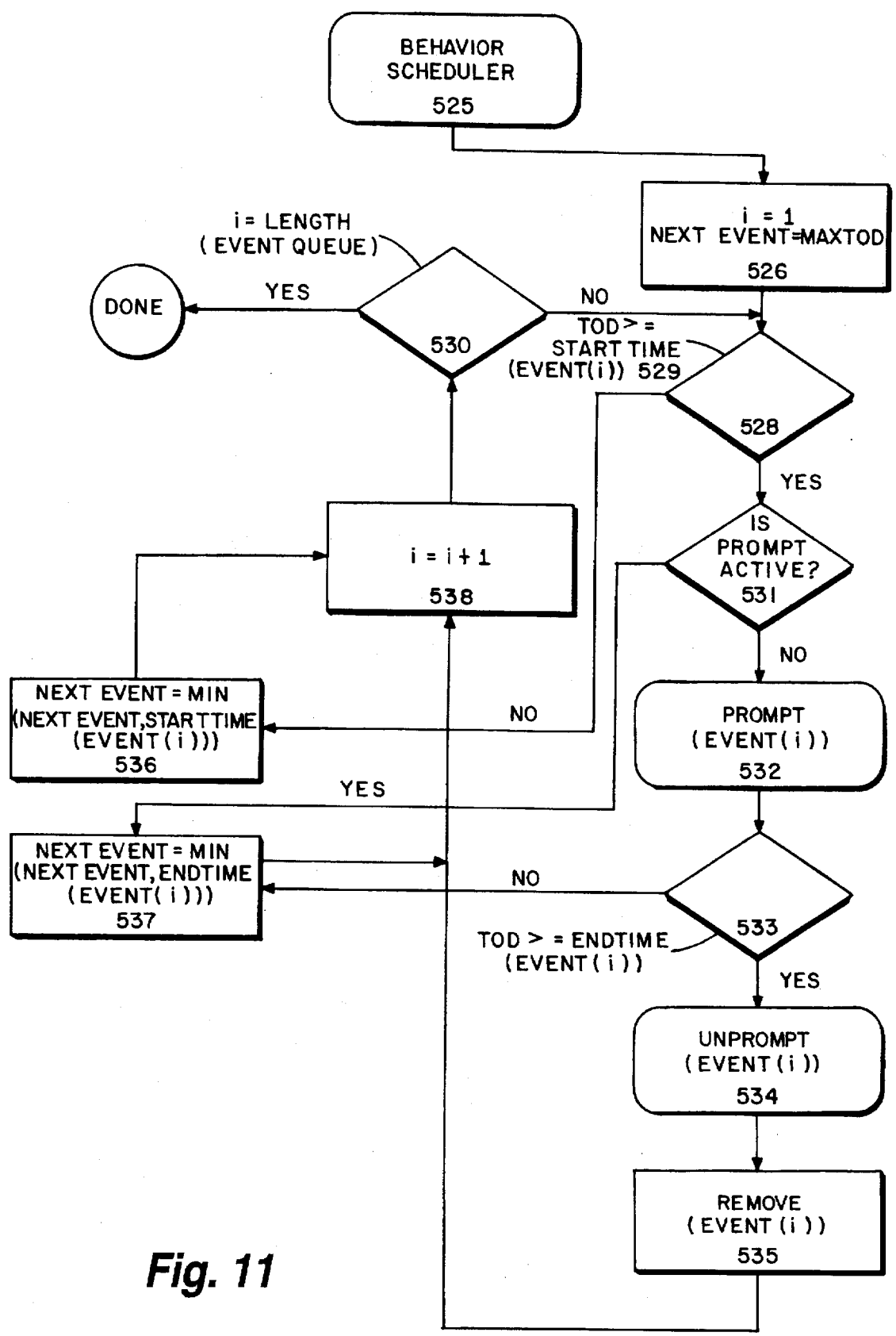
FIG. 11 is a flowchart for the Behavior Scheduler routine.

FIG. 11 is a flow chart of the Behavior Scheduler routine 525. The Time Manager 1600 calls this routine whenever the time of day and date (TOD) is greater than or equal to the time and date of next event. In the first step 526, a variable (i) is set to 1. This variable is used to index all events in the EventQueue. In addition, the variable NextEvent is set to MAXTOD, a very large number. NextEvent will be used to determine the earliest time for which a next event is to be initiated or terminated. It is used by the Time Manager 1600. A comparison function 528 is performed that checks whether the TOD is greater or equal to the start time of the event. The Start Time 529 function determines the starting time of an event in the EventQueue.

If the TOD is less than the start time of the event, then a logical no results. In step 536, the NextEvent is updated if appropriate and the routine increments the variable (i) at step 538 and checks 530 whether the last (i) has been reached. If (i) equals length (EventQueue), then the Behavior Scheduler routine is completed. If (i) is not the last (i), then the routine returns to check the next event at step 528.

If in 528 the TOD is greater than or equal to the start time of event (i) then the logical compare yields a logical yes and passes the routine to a logical decision step 531 that asks whether the prompt for event (i) is active. If the prompt is active, then the routine proceeds to 537 to update the value of NextEvent, from which it increments (i) at 538 and closes the loop. If the prompt is inactive, then in step 532 the function Prompt(Event(i)) activates the prompt(s) for event (i). This function invokes the Behavior Prompting routine 1200. The next step 533, checks whether the prompt should be removed by invoking the EndTime function that determines the end of the period for the prompted activity. For example, meals are prompted to occur within a two and one-half hour period. When a meal event is set, the start time is set at ½ hour before mealtime and the end time is set at 2 hours after mealtime.

If the end of time for the event has not been reached, then the routine adjusts NextEvent at step 537, if necessary, and increments the variable (i) at step 538 as before. If TOD is greater than the end time for the event, then the event has expired and it is time to remove the prompt. Step 534 calls UnPrompt to remove the prompt from the display using the Behavior Prompting routine 1200. Then the event (i) is removed from the event queue.

f. Personalization Routine

The Personalization routine 600 serves two major functions. First, it obtains personal data and preferences from the user that are used by the BMEX 500 to help the user achieve some behavioral goal or goals. For example, the personal data can include the user's name, sex, age, height, body build type, initial weight, normal activity level, food preferences, exercise preferences, normal times for eating meals, type of work, and whether or not he is a shift worker. Second, the Personalization routine obtains environmental information and preferences from the user that relate to the operation of the invention—for example, date, time, password for security, level of "hand-holding" desired, etc.

The personal data collected by the Personalization routine are stored in the User Database 700 for use by other system routines. Although the Personalization data can be changed by the user, they tend by definition to be fairly static, especially compared to data collected by Behavior Monitoring routine 800 or tracked and analyzed by the Behavior Analyzer 560. The environmental data are stored in the Environmental Database 1900.

Figure 12:
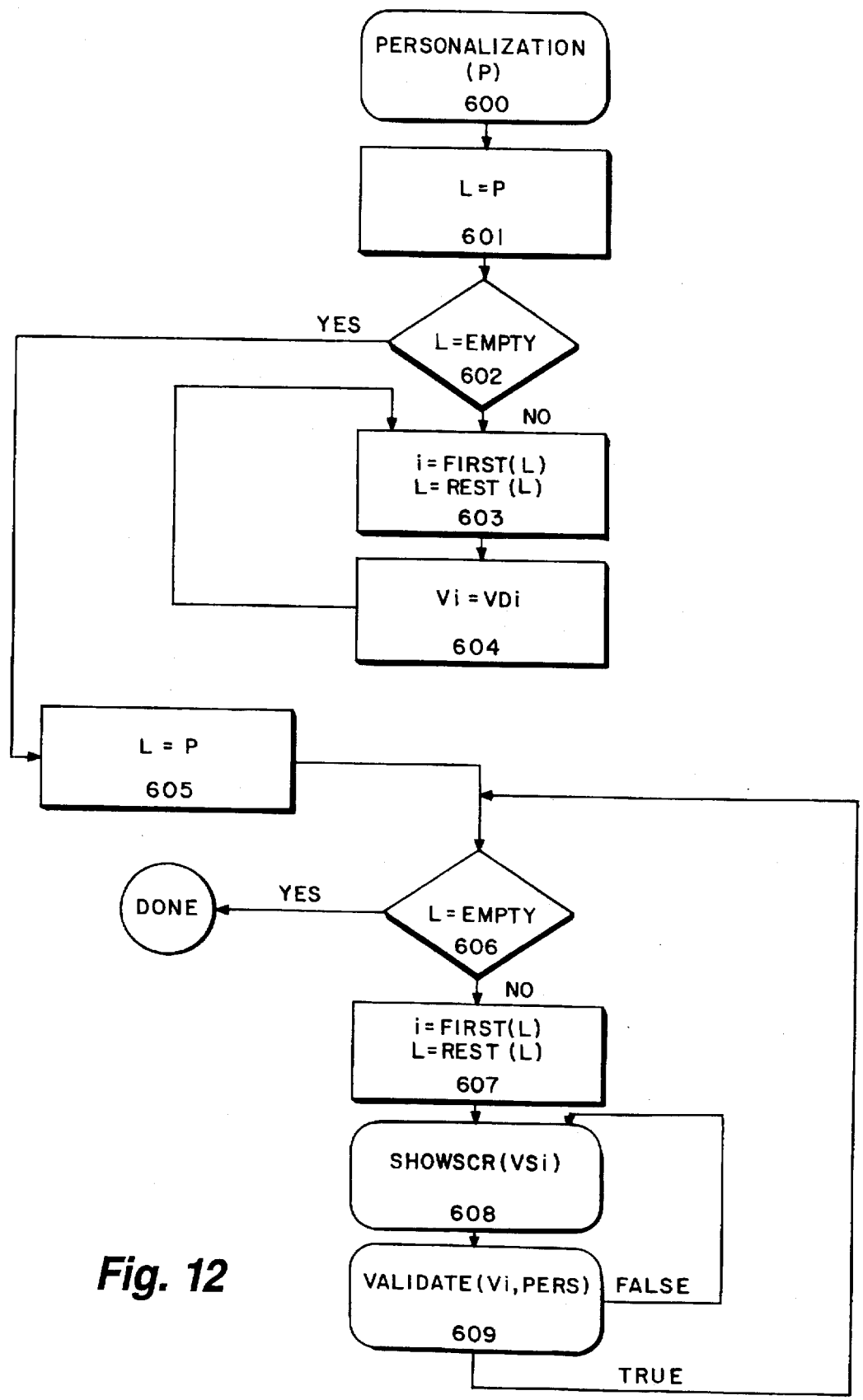
FIG. 12 is a flowchart for the Personalization routine.

FIG. 12 is a flowchart for the Personalization routine 600. The routine is called with an argument P, being the list of variables to be personalized. Including this list is important since subsets of variables can be re-personalized during the operation of the BPGM 510. The routine initially sets a list variable L to P in step 601. There is a set of Personalization variables Vi. In steps 602 through 604, the routine serially sets each variable Vi to a default value VDi obtained from the Subject Matter Database 1100. The loop from 603 through 609 goes through the variables 41 in the list P and solicits values from the user. The user is prompted to enter the values for these Personalization variables by screens described below. The screens are selected by the Personalization routine in step 608 by invoking the Show Screen (ShowScr) function. ShowScr(VSi) displays through the User Interface 1700, the screen VSi, which is the first in the sequence that solicits values for variable Vi. The user enters a value(s) in response to the screen as described below. The validation function in step 609 checks that each value Vi entered by the user is within certain limits. If the validation function indicates that a variable is outside these limits, then the user is prompted to enter another value for that particular variable.

If the validation function indicates that the variable value is valid in step 609, then the Personalization routine checks whether the last variable (i) has been reached in step 606. If not, then the routine allows the user to enter additional information. Otherwise, the Personalization routine is completed and the User Database and Environment Database now have complete personal information on the user.

Figure 13:
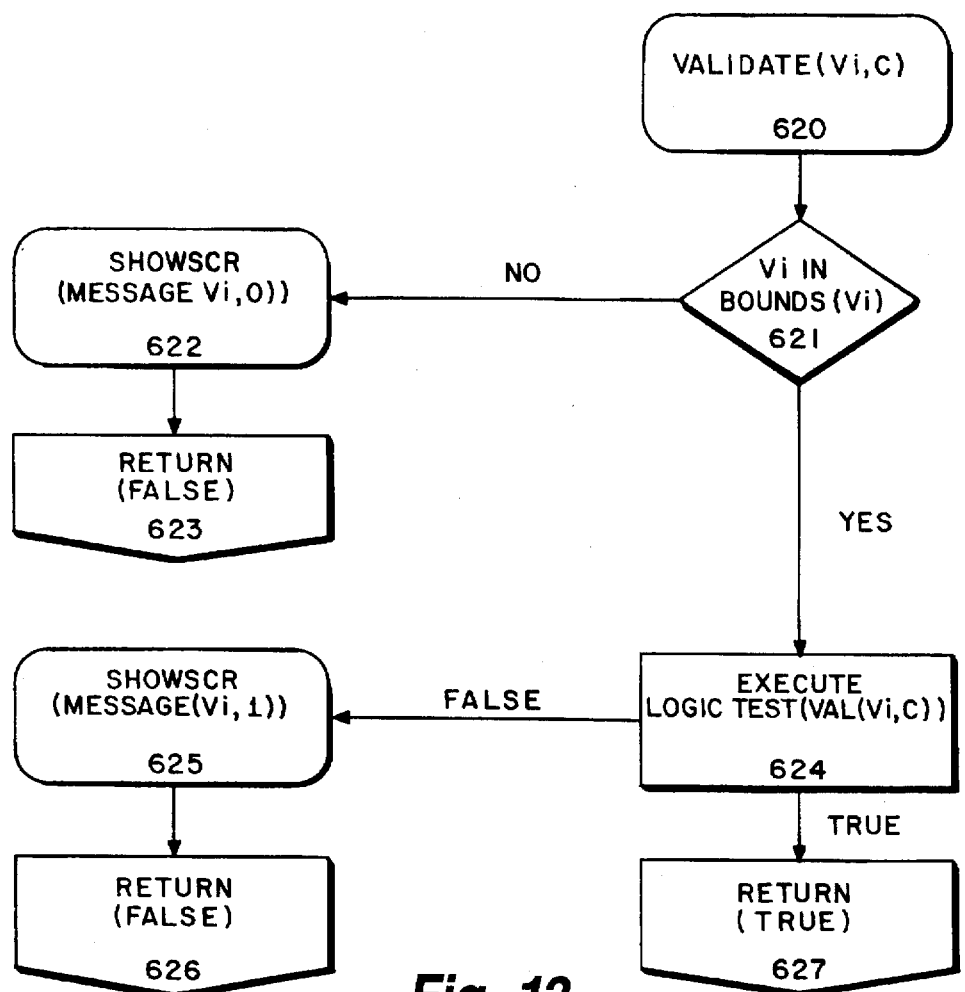
FIG. 13 is a flowchart for the validation function routine.

FIG. 13 shows the validate function 620 executed by the Personalization routine 600. Validate is used to validate the value of the variable Vi in the context C. Validate is used above in context "Personalization," but can be used with other contexts in other routines. The first step 621 of the validate function determines whether the entered value for Vi is within the bounds or limits for that variable set in the Subject Matter Database. If the value is outside the bounds or limits, then the function performs step 622 to show a screen (ShowScr) that presents a message that states the entered value is outside the limits. The message is selected from the library of messages in the Subject Matter Database. Then the validate function returns the value false 623, i.e., not "OK", to the calling function.

If the variable value is within its limits, then step 624 executes a logic test Val(Vi,C) which validates the value of variable Vi in the context C. Val is an arbitrary predicate and can use any available information. For example, if Vi is height, Val (height, Pers) might check the validity of height as a function of age and sex. The logic test yields a true or false value. If the test is true, then the validate function indicates that the variable value is "OK" by returning the value true in step 627. If the logic test is false, then the validate function moves to step 625 that invokes the ShowScr function to present the user with a message that the value Vi entered is not valid. Once the message is displayed, the validate function returns control to the calling routine with a value of False.

g. Time Manager Routine

The Time Manager 1600 maintains time, date, and day-of-week based on the real-time clock input. The initial date and time are set by the user as part of Personalization 600, and may be changed by the user at any time (e.g., change in time zone). The Time Manager is used by several other routines to determine when a new day starts, based on knowledge of the user's wake-work-sleep cycle, and the current time and day-of-week. It handles relevant aspects of the user's life situation (e.g., shift work, and changes in work schedules).

Figure 14:
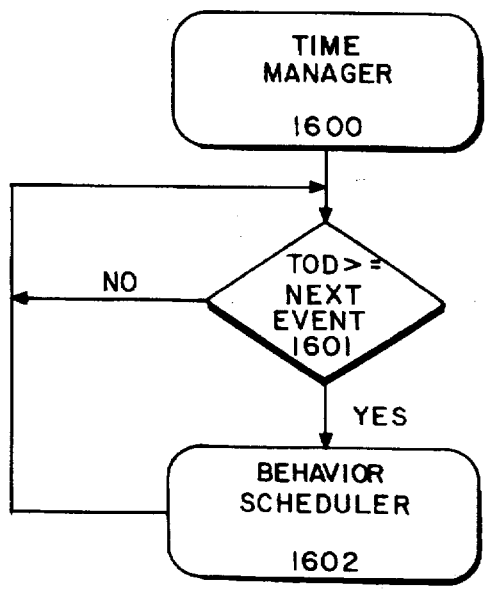
FIG. 14 is a flowchart for the Time Manager routine.

FIG. 14 illustrates the Time Manager 1600. There is a real-time clock external to the Time Manager which operates continuously and sets TOD. TOD is a number which reflects the current day, date and time. Any time TOD is referred to, it is expected to be the most current value. The Time Manager runs all the time and constantly compares the current TOD with the time set in NextEvent. NextEvent is the time for the next planned event in the EventQueue. This event can be a behavioral event, such as breakfast or exercise, or a "housekeeping" event, such as Beginning of Day.

The comparison at step 1601 continues until time equals or exceeds NextEvent. When this occurs, the Behavior Scheduler 525 is invoked to deal with the event. The Behavior Scheduler resets NextEvent as appropriate.

h. Behavior Monitoring Routine

The Behavior Monitoring routine 800 records user behavior using information entered through the User Interface 1700, and provides this data to the Behavior Analyzer 560. The Behavior Monitoring routine records both scheduled behavior (e.g., eating meals, doing exercise, weighing oneself, taking some relaxation time) and unscheduled behavior (e.g., eating snacks, doing extra exercise, drinking water).

For scheduled behavior, the Behavior Monitoring routine operates in conjunction with the Behavior Scheduler 525 and the Behavioral Recommendations routine 1000 to anticipate the user's behavior and, thus, select appropriate display screens that make it easy for the user to record when he has engaged in that behavior. For unscheduled behavior, the Behavior Monitoring routine provides various alternatives through the user interface to allow the user to record such behavior.

Figure 15:
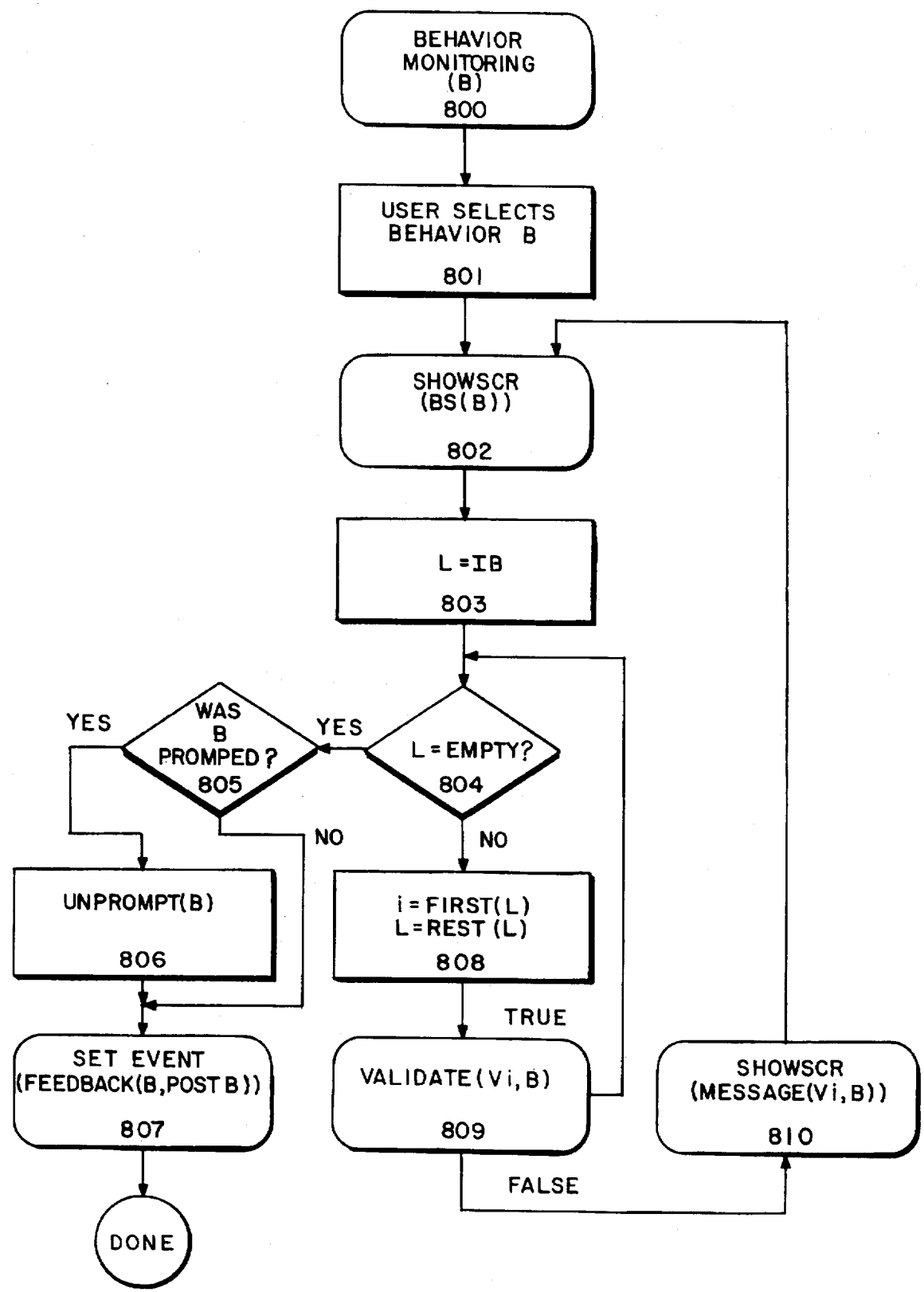
FIG. 15 is a flowchart for the Behavior Monitoring routine.

FIG. 15 is a flowchart of the Behavior Monitoring routine 800. The user registers and records each occurrence of a monitored behavior. At step 801 the user selects a particular behavior B to record. For each behavior, there is a screen BS(B) that corresponds to that behavior and is displayed at step 802. That screen is displayed if the Behavior Scheduler prompted the user to perform the behavior or the screen may be selected by the user to record an unscheduled behavior. The appropriate behavior screen prompts the user to enter the data needed to record the behavior. These data may include several variables.

Each behavior B corresponds to a set IB of variables Vi. The routine collects the data entered by the user in response to the screens. The information entered by the user is recorded as the variable values for the selected behavior.

At step 803, the list L is set to the value IB, the set described above. If L is not empty 804, control passes to step 808 which chooses the first variable in the list.

For each recorded variable in list IB, the Behavior Monitoring routine applies a logic test 809 using Validate(Vi, B) routine that checks the entered data. For example, if the user erroneously enters that his weight changed by fifty pounds in a single day, then the logic test returns the value false. A false value causes a screen to be displayed to the user with message 810 indicating that the keyed data appears to be incorrect. For example, the message may state "Did your weight really change as much as fifty pounds since yesterday?" The routine returns the user to screen in step 802 to reenter the user's behavior.

Once all of the variables have been entered and verified, the Behavior Monitoring routine finds that the list of variables L is empty 804 and checks 805 whether a prompt was displayed for the newly recorded behavior. If the behavior had been prompted, then the prompt is removed 806 from the display. Finally, a subroutine SetEvent(B, Post) is invoked 807 to place the Post Behavior feedback event for behavior B into the scheduler queue. This will cause the Behavior Scheduler 525 to display a feedback message for the recorded event if appropriate.

The Show Screen function is described in the related application Ser. No. 07/639,424 entitled "A Simplified User Interface For A Computer," referenced above and incorporated by reference.

i. Goal Setting Routine

The Goal Setting routine 900 interacts with the user to establish one or more Behavioral Goals. The Behavioral Guidance and Safeguards routine (545) provides information on target goals and allowable goals, as well as rates of achievement in order to help the user set appropriate goals. The Goal Setting routine uses this information to suggest possible goals to the user (e.g., goal weight), suggest time frames for goal achievement (e.g., lose 15 pounds in 10 weeks), and disallow risky goals or rates of achievement (e.g., a weight goal that is too low or a loss rate that is too high). If the user selects a long-range goal, the Goal Setting routine may suggest interim, short-term goals to optimize the chances of success.

Figure 16:
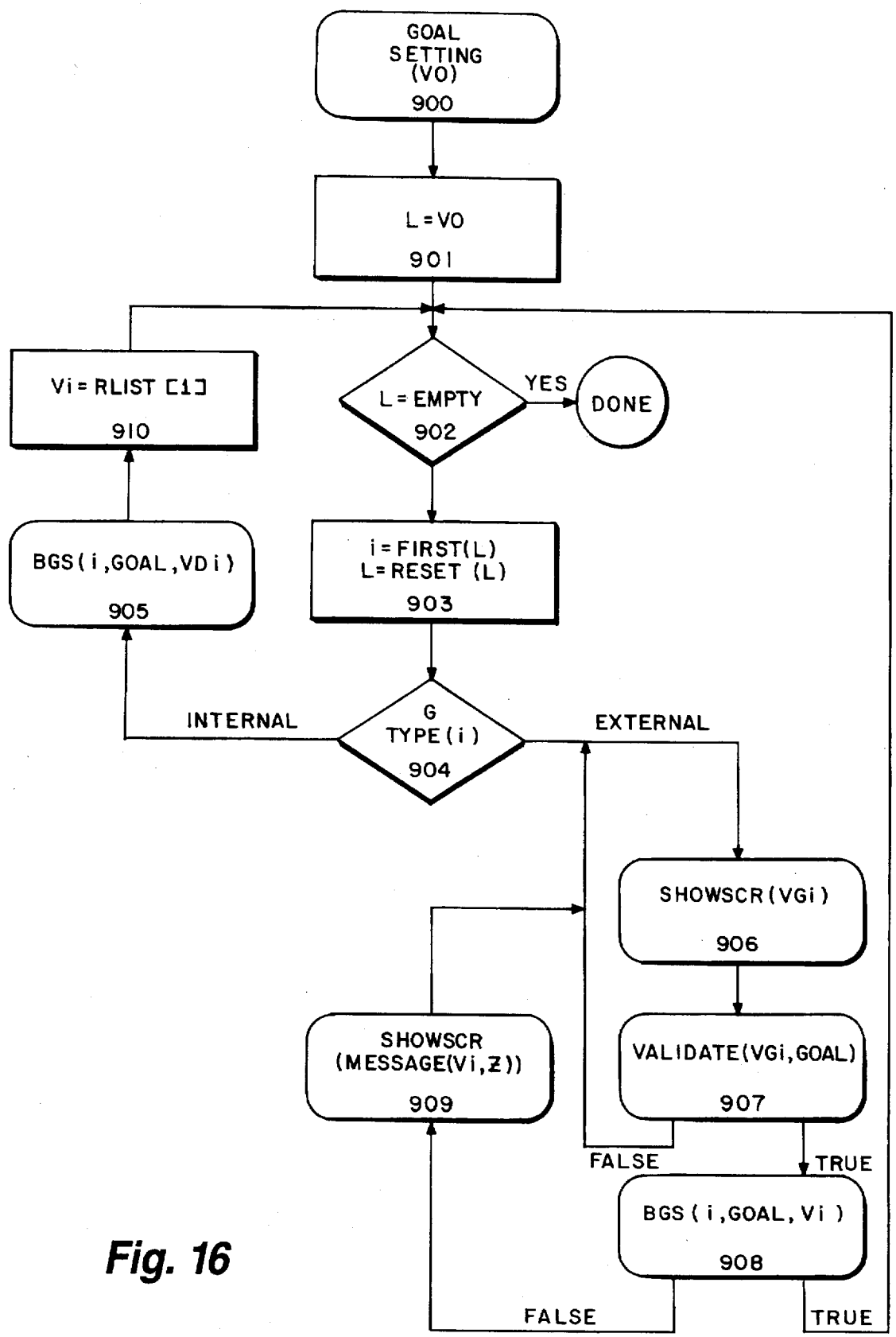
FIG. 16 is a flowchart for the Goal Setting routine.

The flowchart for Goal Setting 900 is shown in FIG. 16. Goal setting is called with a parameter VO, the list of indices of variables for which goals are to be set.

At 901 the temporary variable L is set to VO, the list of variable indices. Step 902 tests if L is empty. If so, the task is complete. Otherwise, the variable i becomes the first item in L and L is truncated by 1 item, in step 903.

Step 904 tests whether the goal type of variable is "internal" or "external," using the Gtype predicate. If it is internal, it is set automatically by the system. Step 905 does this by calling on the Behavior Guidance and Standards routine 545. Then, the BGS recommended value is used to set Vi. Flow returns to step 902 to look for the next item.

If the goal variable Vi is external, then the user can participate in its setting. At step 906, the screen VGi is displayed. This is the first screen in the sequence to solicit user input for the goal variable (i). Next, in step 907 the entered value is validated. If it is found not to be valid, control is returned to step 906 to solicit the user to reenter the value. If valid, the new value is subjected to review by the Behavioral Guidance and Safeguards (BGS) 545 at step 908. Upon successful review, execution goes to step 902 to see if there are further items to process. Otherwise, if the BGS returns a false value, an error message is issued at step 909, and a new attempt to solicit user input is made by going to step 906.

j. Behavior Planning Routine

The Behavior Planning routine 1500 allows the user to plan ahead for behaviors they will perform in the future. It allows the user to indicate exactly what variations of future recommended behavior he plans to select (e.g., which of several possible meals he plans to eat tomorrow).

The Behavior Planning routine offers a number of advantages. If the user has planned which meals he will select from a set of future recommendations, then the planned meals can be presented in such a way as to make selection and recording of the meals simple and quick. Also, meal planning allows the Behavior Planning routine to build a shopping list for the user to ensure he will have the necessary food on hand to prepare planned meals.

Behavior planning in weight loss can be meal planning or exercise planning. Advance meal planning is considered by weight loss experts to be an important aspect of a total weight management program. The objective is to create lists of meals for each day in the planning period, which can be up to 14 days. Creating a meal plan can be done either meal-by-meal or automatically. In the former case, the user selects a day and then a meal (e.g., lunch) for that day. He is then given a choice of all appropriate meal menus, and given the opportunity to examine the contents of each menu. Upon selection of a meal menu, that meal is recorded in an array for planning which is saved in the User Database 700.

With automatic planning, the Behavior Planning routine takes the prior week (7 days) of meals and repeats them, meal for meal, day by day, for the next two weeks. This includes the possibility of planning restaurant meals as well as home meals. Automatic planning is especially convenient for a user who eats the same thing on the same day every week, e.g., pizza for dinner on Friday, roast chicken on Tuesday, etc.

An additional aspect of meal planning is the creation of a shopping list. This is also done by the Behavior Planning routine 1500. A shopping list is created by examining all planned meals in turn. For each meal eaten at home, the menu is retrieved and analyzed. Each item on the menu is noted and the quantities are added to a global count for that item. In the case of items which are composed of other items, the global count is extended one step further. At the end, the user is presented with a list of all items used in all planned menus, with a cumulative total of the quantity required. In data processing terms, this is a classic "Bill of Materials Explosion." While creation of a shopping list and meal planning functions are complex, they are straightforward for any competent programmer to implement.

k. User Database

The User Database 700 stores personal data and preferences obtained through the Personalization routine 600 and historical data of behaviors recorded by the Behavior Monitoring routine 800 and the Behavior Analyzer 560. The specific data collected and stored depends on the behaviors being managed and the particular behavioral goals, although certain data are likely common across most applications (e.g., sex, age, name).

The variables (short-term and long-term) in the User Database below are stored in the RAM 134 of the computer.

Short-Term Variables

The short-term variables are maintained for the current day and the prior 14 days. Indices run from 0 to 14. Day 0 is today, day 1 is yesterday, and so forth.

| | | |
|---|---|---|
| MEAL | DIM(4,15) | Number of times user recorded meal k on day i |
| MM | DIM(4,15) | Menu number for meal k on day i |
| MMT | DIM(4,15) | Menu type for meal k on day i |
| | | 1  Home |
| | | 2  Restaurant |
| | | 3  Exchange |
| | | 4  Calorie |
| MRT | DIM(3,15) | Menu sub-type for meal k on day i |
| | | Restaurant:  Home: |
| | | 1  American  Cookbook |
| | | 2  Chinese  Frozen |
| | | 3  Fast Food  Quick & Easy |
| | | 4  French |
| | | 5  Greek |
| | | 6  Italian |
| | | 7  Japanese |
| | | 8  Mexican |
| | | 9  Seafood |
| MCAL | DIM(4,15) | Calories for meal k on day i |
| MTCAL | DIM(15) | Target calories for day i |
| MFCAL | DIM(4,15) | Fat calories for meal k on day i |
| MSB | DIM(15) | Logical: MSB[i]=1 if any meal on day i had a substitution or change. |
| MK | | Meal index indicating meal most recently recorded |
| | | 1  breakfast |
| | | 2  lunch |
| | | 3  dinner |
| | | 4  snack |
| WI | | Water interval index indicating most recent water interval in which drinking water was recorded |
| | | 1  morning |
| | | 2  afternoon |
| | | 3  evening |
| W | DIM(15) | Weight (pounds) |
| EX | DIM(4,15) | Exercise |
| | | EX[1,i] is exercise type on day i |
| | | EX[2,i] is exercise calories day i |
| | | EX[3,i] is 1 if prompted else 0 |
| | | EX[4,i] is exercise caloric target |
| H2O | DIM(4,15) | Water - Drinks reported on day i |
| | | H2O[1,i] is count in interval 1 |
| | | H2O[2,i] is count in interval 2 |
| | | H2O[3,i] is count in interval 3 |
| | | H2O[4,i] is count outside intervals |
| PMM | DIM(4,15) | Menu number for planned meal k on day i |
| PMMT | DIM(4,15) | Menu type for planned meal k on day i |
| PMRT | DIM(4,15) | Menu sub-type for planned meal k, day i |
| SLIST | DIM(150,5) | Shopping list |
| | | SLIST[i,1]  Checkmark |
| | | SLIST[i,2]  Shopping category |
| | | SLIST[i,3]  Quantity |
| | | SLIST[i,4]  Units |
| | | SLIST[i,5]  Food item |

Long-term Variables

| | | |
|---|---|---|
| NAME | STRING | Name of user |
| WGOAL | | Weight goal (long-term) |
| WGOALST | | Weight goal (short-term) |
| WGOALDT | | Date WGOAL was set |
| WGOALSTDT | | Date WGOALST was set |
| WRATE | | Current loss rate goal (lbs/week) |
| WGINIT | | Weight when WGOALST was set |
| LASTW | | Last weight entered by user |
| SMODE | | Snack mode toggle |
| MT | DIM(4,2) | Mealtimes (target) |
| | | \| Daily \| Weekend |
| | | Bkfst \| xx:xx \| xx:xx |
| | | Lunch \| xx:xx \| xx:xx |
| | | Dinner \| xx:xx \| xx:xx |
| | | Snack \| xx:xx \| xx:xx |
| LASTDT | | Last date user recorded anything |
| FBSDATE | | Feedback start date |
| INITDT | | Date first personalized by current user |
| PERSDT | | Date most recently personalized |
| SLDATE | | Date shopping list was created |
| HT | | Height (inches) |
| SEX | Boolean | 0 =[0 female; 1 = male |
| BDATE | | Date of birth |
| ACTLEVEL | | Activity level |
| DPHASE | | Diet phase |
| EXLISTP | DIM( ) | Exercise choices. 1 corresponding to items in EXLIST chosen by user. Other entries are 0. |
| EXFLAG | Boolean | Set to 1 if user exercised during baseline period and has not exercised since |
| EXDT | | Exercise target for number of days per week to exercise |
| STDATE | | Date of first use on current program |
| STTIME | | Time of first use on current program |
| EXCHTOG | Boolean | Determine whether meal recording using using calories or exchanges is permitted. |
| AVGRATE | | Average weighted rate of weight loss |
| LASTRWL | | Last week's evaluated weight loss rate |
| LASTWTL | | Last week's evaluated weight level |
| MAXWLR | | Maximum allowable weight loss rate |
| NWNP | | Number of weeks of no progress |
| NWP3 | | Number of weeks in Phase 3 |
| NWRL | | Number of weeks of rapid weight loss |
| PROBLEM | Boolean | Equal to 1 if problem condition (either too rapid weight loss or no progress) already encountered this week. |
| PTOL | | Problem tolerance around weight goal |

The following long-term variables are calculated weekly for 2 years (104 items each)

| | | |
|---|---|---|
| LW | DIM(105) | Weight. LW[0] is initial weight. |
| LWB | DIM(104) | Number of times user entered weight that week |
| LCAL | DIM(104) | Calories (weekly total) |
| DTCAL | | Target calories (daily) |
| LWTCAL | DIM(104) | Weekly total of daily target calories |
| LFCAL | DIM(104) | Fat calories (weekly total) |
| LEX | DIM(104) | Exercise calories (weekly total) |
| LTEX | DIM(104) | Target exercise calories (daily) |
| LEXCT | DIM(104) | Number of days with some exercise |
| LWI | | Number of weeks on the program |
| LWIDT | | Date LWI was last updated |
| MTYPE | | Menu type for current transaction |
| RTYPE | | Menu sub-type for current transaction |
| CHANGETOG | Boolean | Menu has been changed |
| CHANGEITEM | | Menu item currently being changed |
| SUBFOOD | | Food being substituted |
| MENUNO | | Menu number |
| CAL | | Calories in meal being recorded |
| FATCAL | | Fat calories in meal being recorded |
| EXCHOICE | | Exercise choice |
| EXTIME | | Time (minutes) for current exercise |
| NSHOP | DIM(4) | NSHOP[i] is number of people to shop for meal i. |
| HMEALCT | DIM(4) | HMEALCT[i] is number of home meals planned for meal i. |
| DAYCT | | Number of meals planned for (total) |
| DAYTOG | Boolean | Meal is planned for current day |
| BASE | | Total caloric expenditure during base period |
| BDAYS | | Number of days that user exercised at least to minimum level during base period |
| MAX | | Maximum target for caloric expenditure from exercise |
| MIN | | Minimum target for caloric expenditure from exercise |
| NDAYS | | Number of days elapsed in week so far |
| DAYCAL | | Projected daily caloric level |
| DIFCAL | | Project caloric adjustment |
| MAXWLG | | Maximum short-term weight loss goal |

-continued

| | | |
|---|---|---|
| MINWLG | | Minimum short-term weight loss goal |
| PWL | DIM(8) | Projected weight loss from now to week (i) |
| SWN | | Starting week number |
| WLR | | Projected weight loss rate |
| LT | | Last mealtime affected by time change |
| CALALE | Boolean | Equal to 1 if caloric intake has been at or below minimum caloric level |
| DAYNO | | Day number (0 to 6) in user's week (based on day user started the program |
| EXCAGE | Boolean | Equal to 1 if exercise compliance has been at or above prescription |
| NWKS | | Number of weeks for which user is not considered to be progressing |
| WTCNT | | Counter of number of weights entered so far this week |
| WTSUM | | Sum of weights entered so far this week |

1. Environment Database

The Environment Database 1900 stores information relating to the operation of the unit, including time, date, user interaction level, and personal identification number (PIN).

The following items are stored in the Environment Database 1900.

| | | |
|---|---|---|
| PIN | | Personal identification number (password) |
| TODAY | | Date on which the most recent Beginning of Day processing was performed |
| CONTRAST | | Screen contrast. |
| BATTMESS | Boolean | Battery Low message needs to be delivered. | m. Subject Matter Database

The Subject Matter Database 1100 stores medical, scientific, nutritional and other relevant data related to the behaviors of interest for a particular application. For example, for a weight management application, the following information are stored: nutritional data for various foods; meal menus for nutritionally balanced breakfasts, lunches, and dinners; common food substitutions; a selection of "healthy" snacks; and the number of calories burned per unit time for different forms of exercise.

The items in the subject matter database are stored in the ROM 160 of the computer, as follows:

| | | | | | |
|---|---|---|---|---|---|
| MNAME | STRING(4,2) | Meal name | | | |
| | | breakfast | Breakfast | | |
| | | lunch | Lunch | | |
| | | dinner | Dinner | | |
| | | snack | Snack | | |
| RLIST | STRING(3,) | Restaurant type list - by meal. Table I below indicates which entries exist in RLIST for which meal type. | | | |
| | | TABLE I | | | |
| | | RLIST | Bkfst | Lunch | Dinner |
| | | American | 1 | 1 | 1 |
| | | Chinese | 0 | 1 | 1 |
| | | Fast Food | 1 | 1 | 1 |
| | | French | 0 | 1 | 1 |
| | | Greek | 0 | 1 | 1 |
| | | Italian | 0 | 1 | 1 |
| | | Japanese | 0 | 1 | 1 |
| | | Mexican | 0 | 1 | 1 |
| | | Seafood | 0 | 1 | 1 |
| EXLIST | STRING( ) | Exercise list | | | |
| EXDATA | DIM( ,3) | Exercise parameters | | | |

-continued

| | | |
|---|---|---|
| | | Factor |
| | | Cluster |
| | | Cluster priority |
| DDMT | DIM(4,2) | Default meal times (MT) |
| MPCT | DIM(3) | Target percentage of daily calories for each main meal. Currently: 25, 35, 40. |
| SCAT | STRING( ) | Shopping categories |

Food Tables

The tables described below contain the Food Database of the Subject Matter Database. The tables are described in relational terms.

Compound Food Yield Table

This table shows the yield of a compound food's recipe.

1. Compound Food ID
2. Yield

Compound Food Table

This is a repeating group table which contains a record for each simple food item which is used to make a compound food item.

1. Compound Food ID
2. Food ID
3. Food Order
4. Unit Factor

Equivalent Food Chain Table

This table is a list of equivalent food items.

1. Chain Identifier
2. Food ID

Food Item Table

This table contains a record for each unique food item used in the menus stored in the Subject Matter Database. It stores nutrient data used in analysis of the menus.

1. Food ID
2. Food Name
3. Units Eaten Code
4. Chain Identifier
5. Shopping Category ID
6. Compound/Simple Flag
7. Calories/100 Grams
8. Gram Weight
9. Fat
10. Saturated Fat
11. Polyunsaturated Fat
12. Monounsaturated Fat
13. Protein
14. Carbohydrates
15. Dietary Fiber
16. Cholesterol
17. Sodium
18. Sugar
19. Calcium
20. Iron
21. Copper
22. Zinc
23. Magnesium
24. Phosphorus
25. Potassium
26. Iodine
27. Selenium 28. Thiamine
29. Riboflavin
30. Niacin
31. Folacin
32. Vitamin A
33. Vitamin B6
34. Vitamin B12
35. Vitamin C
36. Vitamin D
37. Vitamin E
38. Water Meal Type Table This table stores the Meal Type codes and their associated descriptions.

1. Meal Type
2. Meal Name

Menu Name Table

This table stores the basic unique data pertaining to each menu.

1. Menu ID (MENUNO)
2. Menu Name
3. Meal Type
4. Menu Type
5. Menu Sub-Type

Menu Sub-Type Table

This table stores the Menu Sub-Type codes and their associated descriptions.

1. Menu Sub-Type
2. Menu Sub-Type Name

Menu Table

This is a repeating group table which contains a record for each food item in a menu. For each food item, there are 5 different quantities stored which correspond to the 5 different caloric levels.

1. Menu ID (MENUNO)
2. Food ID
3. Food Order
4. Quantity 1200
5. Quantity 1500
6. Quantity 1800
7. Quantity 2100
8. Quantity 2500

Menu Type Table

This table stores the Menu Type codes and their associated descriptions.

1. Menu Type
2. Menu Type Name

Shopping Category Table

This table contains records of various shopping/grocery store food categories/aisles.

1. Shopping Category ID
2. Shopping Description
3. Shopping Sequence

Units Eaten Table

This table contains records used by the Food Item Table to determine the base unit amount of the food eaten.

1. Units Eaten Code
2. Unit Name

3. Resolution Numerator
4. Resolution Denom.
5. Fluid/Dry n. Behavioral Recommendations Routine The Behavioral Recommendations routine 1000 makes specific recommendations for behavior to be engaged in by the user, and allows the user to make certain modifications to the recommendations prior to recording that behavior as completed.

For example, the information generated by the Behavior Analyzer is used by the Behavioral Recommendations routine to select specific recommended behaviors (e.g., which set of lunch menus to suggest, which exercise should appear first in a list of recommended exercises). Once the user is presented with a recommendation, he is allowed to make modifications to it (e.g., substitute food items in a meal, change quantities of food in a menu, enter his lunch meal in terms of total calories rather than choosing one of a set of recommended menus).

The Behavioral Recommendations routine 1000 is best described verbally, this level of description is sufficient for a programmer of ordinary skill to reproduce it. The context of the description will be for recommending and recording meals, but is easily generalized to other behaviors.

The user begins to record a meal either spontaneously or after being prompted by Behavior Prompting 1200. The recording is done via Behavior Monitoring 800. The screen invoked in 802 of Behavior Monitoring can trigger Behavior Recommendations. Upon choosing the meal to be recorded at the main screen FIG. 17, he must choose at FIG. 18 whether to eat a meal at home or in a restaurant. In the event there was a meal planned for this day and this particular mealtime, the highlight would have been on the item Planned Meal. In the case of a planned meal being selected, the next two steps are skipped and the chosen planned menu is displayed directly. Otherwise, the user is offered a choice of meal sub-types (FIG. 19 for home menus, with a similar screen of restaurant types being presented for restaurants). Next, FIG. 20 displays the first screen of a list of all the recommended meals of the chosen type and sub-type. On selecting a menu name, the actual menu FIG. 21 is displayed.

When the menu is displayed, it has been chosen to have the correct number of calories. This is determined by the BPGM 510 in conjunction with Behavior Adaptation 575, based on the Personalization variables and the behavior history stored in the User Database 700. The composition and proposed quantities of each menu vary as a function of the recommended calories.

The caloric content and percentage of calories from fat are displayed in a pop-up window FIG. 22 and the user is given the choice of next actions in FIG. 23. The simplest choice is to record the meal directly, in which case the system returns to the main screen FIG. 17. Alternatively, the user can choose to substitute a food. Thus, a user can alter the recommendations, but only within acceptable constraints.

The Subject Matter Database 1100 contains, in addition to complete information about menus and foods, a set of substitution or equivalence tables. These provide lists of foods which are nutritionally similar to each other. Each food in the system has a designated equivalence class which refers to these tables. When the user chooses a substitution in FIG. 23, he is presented with a screen(s) FIG. 24 of the items in the substitution list for the chosen food. The quantities in front of each food are adjusted to provide a portion with approximately the same number of calories as the original item in the menu. Once the user chooses an item, it is substituted into the original menu FIG. 25. FIG. 26 displays the caloric content of the menu after the changes. From here the user returns to FIG. 23 to make further changes or to record his meal with changes.

A second kind of change to the recommended meal is to alter the quantity of an item on the menu. This is done by selecting the item to change and then changing the quantity on the screen as shown in FIGS. 40 and 41. As before, this is replaced into the original menu and can be recorded from the screen in FIG. 23.

o. Behavior Feedback Routine

The Behavior Feedback routine 1300 tells the user how he is doing, gives him reminders and encouragement, gives suggestions on how to improve, and provides information and educational material that will help them achieve his goals. The Behavior Feedback routine operates in conjunction with the Behavioral Analyzer to determine which aspects of the user's behavior would benefit from feedback, and then the Behavior Scheduler determines when to give feedback.

Feedback messages are varied in form and content to keep the user's interest and to avoid repetition, as was discussed in detail earlier. A library of messages is stored in the Subject Matter Database and categorized in the database by the type of message. When a message type is selected by the feedback routine, a particular message from the category for that selected type is presented to the user. By varying the messages, the user does not become bored with the feedback messages.

The Feedback routine 1300 itself is simply a presentation mechanism, using standard techniques to present information via the user interface 1700.

p. Miscellaneous Routines

The Progress Reporting routine 1400 provides tables and graphs showing the user progress based on historical data stored in the User Database 700 and processed by the Behavior Analyzer 560. The user can at any time request to see tables and graphs showing his progress by invoking the Progress Reporting routine.

The Behavior Prompting routine 1200 gives users prompts for recommended behavior via the User Interface 1700. It is invoked by the Behavior Scheduler 1200. Prompts are repeated as necessary, possibly in varied forms, until the user responds as recommended. The forms in which prompts occur include text, audio signals, and voice output. As with feedback and progress reporting, prompting is a straightforward presentation via the User Interface and is well within the ability of those with ordinary skill in the art.

The User Interface 1700 manages user input and output based on the available controls and display capability. It implements all interactions, including limited keys form of alphanumeric input, and handles pop up windows and audio signals. In addition, it provides an extensive context-sensitive user help facility. The User Interface is described in more detail in patent application Ser. No. 07/639,424, entitled "A Simplified User Interface For A Computer."

The Input/Output devices 1800 are the particular interface hardware of the device. In the preferred embodiment, the Input/Output hardware is a nine button keyboard and a liquid crystal display segregated into a prompt area and a text area. It is contemplated that Input/Output devices could also include push buttons, keyboards, display screens, touch-sensitive screens, pointing devices (e.g., mouses, trackballs) audio, video, graphics, control knobs, voice recognition, voice output, interfaces to sensors and transducers (e.g., scales, heart and pulse monitors, blood samples, $CO_2$ levels, activity sensors, pedometers), IPC barcode readers, printers or communications links.

IV. Typical User Day Using Computer

The operation of the preferred embodiment of the weight control computer is best described in the context of a typical day of a user. The user must first personalize the programming in the computer by keying in certain characteristics. The user is prompted to begin entering the personalization information by a screen shown in FIG. 27. The computer invokes its Personalization routine 600 to begin a dialogue with the user to obtain the personal data necessary to tailor the program for the individual. For instance, the user's name is used in a number of feedback screens during the program. Sex, birth date, weight, height and activity level are used in the determination of base calories. Accordingly, screens to prompt the user to enter this information are presented to the user. These screens are shown in FIGS. 28 to 32.

Because of the importance of these personal data, the Personalization routine 600 verifies that information has been entered correctly as is shown in FIG. 33. During the dialogue thus far, and in all dialogues between the user and the weight control computer, the system's limited set of nine buttons is used for all user inputs. Since all interactions are either questions or choices, the user can respond appropriately to the computer's request with either Yes and No inputs or by moving the highlight and pressing Go On. The user enters numerical information by repeatedly pressing the up/down keys 15 to change a number and by pressing the Go On/Go Back keys 16, 18 to move the cursor as seen in FIG. 29.

Inputting additional personalization information involves setting of weight goals and loss rates. A screen, FIG. 34, is presented to the user to set or change his weight goal. The computer queries the user regarding his current weight and desired weight, and possibly the amount of weight the user wants to lose short-term.

During all inputs, including those above, the system checks data provided against its database of allowable ranges. Other plausibility checks involving more complex rule-based reviews of related data are also performed. A user whose personal parameters are outside the bounds acceptable to the system will not be able to use it without strong warnings.

The computer can generate some goals itself. In the case of short-term weight goals, the system proposes a goal and allows the user to modify it, within reasonable bounds as is shown in FIGS. 35 and 36.

Other personal data include mealtimes and snacking preferences, as these are the basis for daily prompting and feedback. Accordingly, screens are presented to the user requesting the user to confirm or enter his usual mealtimes, FIG. 37, and whether he wants to include a snack as an additional meal, FIG. 38. Reasonable default values are provided for the user not wishing to enter his own values. In these cases, the user must still confirm use of the proposed default values.

The user's weight loss program is based upon reduced caloric intake and regular exercise. Promoting exercise requires knowledge of the user's exercise preferences and habits. The preferences are requested during the personalization dialogue. As shown in FIG. 39, checkmarks (set with Yes and No) indicate those items which the user prefers to do. This information is used by the computer during the program to prompt and shape the user's behavior.

Once the user has personalized the computer by entering his information into its User Database 700, the user is returned to the main screen, FIG. 17, that is generally the first screen presented to the user once the user has entered the personalization information. The main screen is the "home base" for the program. The computer automatically returns the user to this main screen after each interaction with the computer is completed. A user can always return to the main screen by pressing the Go Back key 18 one or more times or by turning the unit off and then on. On the main screen, the highlighted cursor will be either on the first item or on the item being prompted if any.

As shown in FIG. 18, to choose a meal from the main menu, the user highlights the meal, i.e., breakfast, lunch, dinner or snack, to be eaten and presses the Go On button 16. This gives a choice of where the meal is to be eaten. If a meal had been planned, it can be chosen directly from the next screen. Having chosen a meal type, the user can choose from among a wide variety of menus. As shown in FIG. 19, if the user selects home meals, he can choose meals that are Quick & Easy to prepare, more elaborate meals categorized under a Cookbook category, and Frozen Meals that correspond to commercially available frozen entrees.

As shown in FIG. 20, within any category, e.g., Quick & Easy, From the Cookbook, Frozen Meals, there is an extensive choice of menus. In the preferred embodiment, the Subject Matter Database contains nearly 300 menus, each of which has variations to address the multiple caloric levels which may be required by the total universe of potential users. Even a single user will have varying caloric requirements over the typical period of use, including long-term weight maintenance, that must be taken into account by the computer in recommending the meal.

Having chosen a menu, the user presses the GoOn button to have the menu actually displayed in the manner shown in FIG. 21. The menu shown will be at the appropriate caloric level, taking into account the user's daily caloric requirement, meals already eaten and correct balance of calories by meal. A further press of the GoOn button 16 reveals a window showing the caloric value of the menu, as is shown in FIG. 22. As shown in FIG. 23, depressing the Go On button yet again presents the user with a screen asking if the meal should be recorded or if the user desires the computer to take further action before choosing to record it.

If the meal is recorded, then information regarding the meal is stored in the User Database. The user can alter his meal information before recording it. For example, as shown in FIG. 24, the user substituted a wedge of watermelon for the banana. He can choose among nutritionally equivalent foods, for which the quantities have been adjusted to give a similar number of calories as the originally prescribed quantity of the original food. By choosing watermelon and pressing the Go On button, the watermelon is substituted into the current menu as is shown in FIG. 25. Once the meal has been changed, e.g., by substituting a food, the caloric value of the new menu is displayed as is shown in FIG. 26.

In addition to substituting one food for another, it is possible to change the quantities of foods in a meal that is being displayed by the computer. For instance, the user may decide to have less milk as is shown by comparing FIGS. 40 and 41. The screen presents the user with the option of changing a quantity which in turn allows the user to change the numerical amount, e.g., volume or mass, of the food to be eaten. As with substituting a food, once the quantity of food is changed, the menu is redisplayed to the user with the new quantity and subsequently its caloric value and percentage of calories from fat are displayed.

When it is time to exercise, the user is prompted by the Behavior Prompting routine with an audio prompt and a screen such as shown in FIG. 42. By choosing exercise from the main screen, the user goes to an exercise screen FIG. 42 that displays the exercises previously chosen during the Personalization program, along with the minimal exercise times required to achieve the recommended caloric expenditure. This minimal exercise period is calculated according to the caloric algorithm executed by the BPGM routine 510 and updated as needed by the Behavior Adaptation routine 575. For the early weeks of the program, the BPGM sets the exercise expectations low to allow the user to supply a baseline of his usual frequency and duration of exercise. If the user desires to perform an exercise other than one of those selected in the personalization routine, he can choose other exercises by selecting an "other" menu option, which displays a complete list of other exercises. The selected other exercise can also be added permanently to the list of regular exercises by invoking a changing information option from the main screen.

The exercise related software routines, e.g. BPGM 510 and BGS 545, monitor a user's exercise patterns and warn him of any changes which might be painful or dangerous. If the Behavioral Guidance and Safeguards (BGS) 545 routine determines that an unsafe or inadvisable exercise is to be performed, it in conjunction with the BPGM and the Behavioral Recommendation routine 1000, presents a caution message to the user such as is shown in FIG. 43. Once the exercise is preformed, the user can enter the actual exercise time, through the Behavior Monitoring routine 900, and receive feedback, through the Behavior Feedback routine 1300, on caloric expenditure in response to a screen such as shown in FIGS. 44 and 45.

After an activity, e.g., eating or exercise, is recorded, the Behavior Feedback routine provides behavioral feedback if appropriate. The feedback is designed to reinforce positive actions and provide warnings for negative ones. The feedback generally is in the form of messages selected by the Behavior Feedback routine from the Subject Matter database. An example of a feedback message is shown in FIG. 46.

As FIG. 48 also shows, when the weight control computer is first turned on, the user is presented with screens that show a set of reminders, based on his prior behavior. These reminder messages can be recalled by the user at any time by selecting the Bulletin Board option from the main menu.

From the main screen, the user can select a Bulletin Board option that displays a summary of the user's behavior today, as well as a summary of any outstanding feedback messages. An example of a Bulletin Board display is shown in FIGS. 47 and 48. The Bulletin Board is part of Progress Reporting 1400, which queries the User Database 700.

In addition to simply recording a food menu option displayed on the screen, a meal can be recorded by directly entering the number of calories eaten during the meal or by entering food exchanges. Food exchanges is a system of reckoning nutritional value developed by the American Dietetic Association and American Diabetic Association. Food exchanges are included as an option because many people are familiar with them and have used them in other manual weight loss programs. FIG. 49 shows an example of the screen that allows a user to enter the number of calories eaten during a meal.

By invoking the Behavior Planning routine 1500, the user can call up screens that offer the option of planning meals for the future, up to 2 weeks ahead. This planning option is especially important to dieters because meal planning is a way to ensure that the correct foods will be available when needed. As shown in FIG. 50, a screen is presented that allows the user to create his own meal plan or that instructs the computer to automatically prepare a meal plan. Once the meal plan is created, the user can view screens that show the meal plan and then the user can record the meal plan in the computer. A partial meal plan outline is shown in FIG. 51 which shows that the user has already set up his plans for breakfast (B) and lunch (L) on Thursday, December 20.

In planning a meal, the same kind of dialogue takes place as when choosing a meal to record. As shown in FIG. 52, the user plans dinner for December 20 by first selecting the dinner option from a screen. Upon selecting the dinner option, the user interacts with the computer via a series of screens, such as shown in FIGS. 53 to 56, in which the user chooses to prepare a meal at home, that is somewhat elaborate, i.e., From the Cookbook, and is named Crispy Chicken. Upon selecting Crispy Chicken, a screen appears that shows the entire menu for the planned Thursday December 20 dinner of Crispy Chicken. The user can always choose not to eat this meal on the appointed day, or he can alter a meal he has planned at the time he records it.

Figure 57:
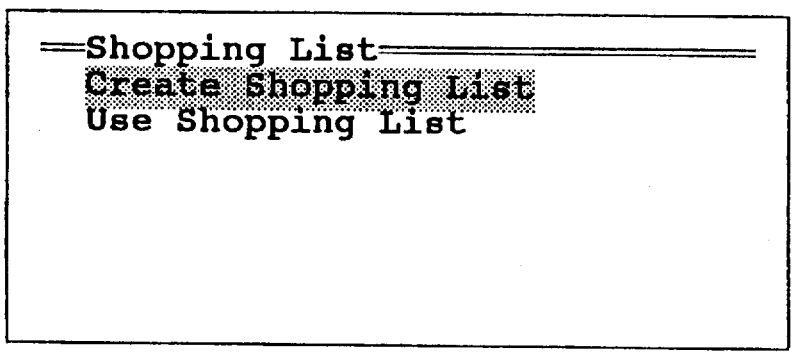
Figure 58:
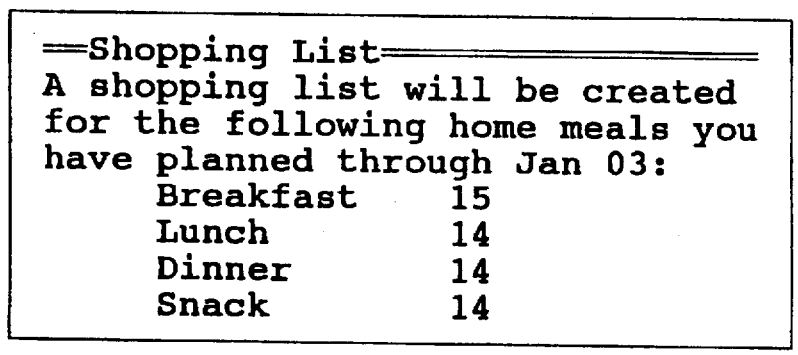
Figure 59:
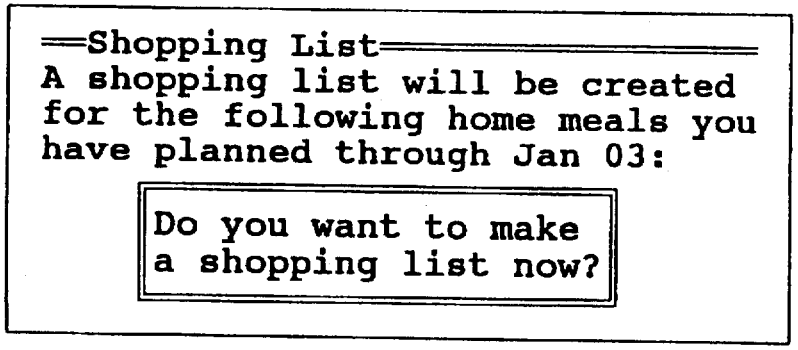
Figure 60:
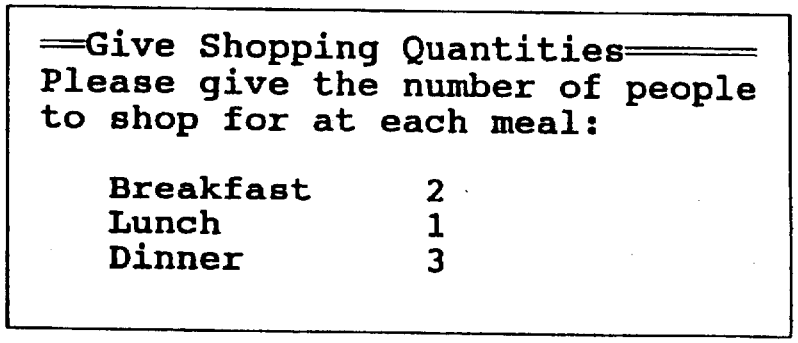

Using the meal plan, one can instruct the computer to create a shopping list of all the items needed to prepare the home meals as shown in FIGS. 57 and 58. The user can enter the number of people who will be eating the planned meals. The shopping list is automatically prepared by the Behavioral Planning routine 1500 and presented to the user via a series of screens that groups the food items to be purchased by common shopping categories for ease of shopping. FIGS. 59 through 65 show examples of the screens that present the shopping list. As the user purchases each item in the grocery store, he records the purchase in the computer which check marks the list.

Figures 65, 66:
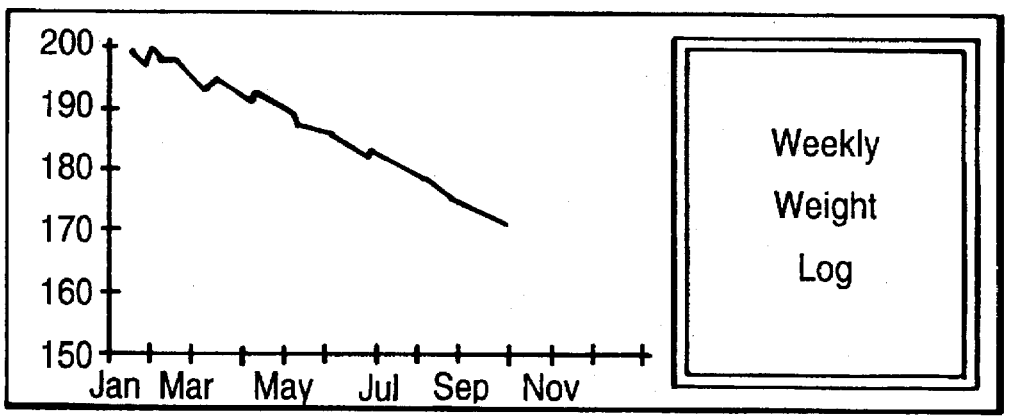

FIG. 66 is an example of the kinds of progress charts that can be obtained from Progress Reporting 1400. It illustrates the user's weight over the past several months. Similar charts are available for calories eaten and exercise calories.

The disclosed preferred embodiment is a weight control computer. However, this embodiment of the invention has a broader application to diet and exercise control. As previously mentioned, this embodiment can be applied to manage a low cholesterol diet, a diabetic's diet, and hypertension control diet. Of course, the embodiment would have to be modified to address particular concerns of the diet, e.g., appropriate menues, display screens and feedback messages. Indeed, any diet and exercise regime can be managed using this embodiment of the invention.

While the invention has been described in connection with what is presently considered to be the most practical and preferred embodiment, it is to be understood that the invention is not to be limited to the disclosed embodiment. On the contrary, it is intended to cover various modifications and equivalent arrangements included within the spirit and scope of the appended claims.

What is claimed is:

1. A behavior management system comprising:
   a self-contained portable hand-held computer having a processor, memory accessible by the processor, and input keys and a display both in communication with the processor;
   personalization means for receiving and storing personal information regarding a user and said user's behavior goals, including the input keys for receiving the personal information and the memory for storing the personal information including information regarding behavior goals;
   said processor including a processing means for generating a behavior management program by accessing said memory to retrieve the personal information, said program prompting the user to perform one or more behaviors, to achieve said behavior goals wherein prompts are generated when the behavior management program determines that the one or more behaviors, are to be performed;
   output means for displaying each of the prompts for said behavior when the behaviors, are to be performed, said output means being operatively coupled to said processing means;
   behavior recording and storage means for recording data regarding behavior and a bodily condition of the user for a period of time extending through several prompts;
   said processor further including an adaptation means operatively coupled to said processing means for receiving via the input keys information regarding the user's recorded behaviors, analyzing the recorded data regarding recorded behaviors and bodily conditions to determine historical trends in behavior and changes in the bodily condition, and dynamically adapting said behavior management program in response to said historical trends and changes in the bodily condition, so that the program will generate new prompts to achieve said behavior goals.

2. A behavior management system as in claim 1 wherein one of said behaviors to be prompted is exercise.

3. A behavior management system as in claim 1 or 2, wherein the input keys receive user behavior information including information regarding foods eaten by the user and weights of the user at different times, and said processor further comprising feedback means operatively coupled to said processing means for providing feedback to the user regarding compliance with said behavior management program or progress towards said behavior goals.

4. A behavior management system as in claim 3 wherein said output means is a display and said feedback is displayed on said display.

5. A behavior management system as in claim 3 wherein said feedback means further comprises the memory in which is stored a database of feedback messages indexed by a set of one or more variables, and accessing means for selecting a feedback message by identification of values for said set.

6. A behavior management system as in claim 3 wherein said feedback means accesses the memory having a database of feedback messages, said feedback messages being categorized by current behavior and by behavior history, said feedback means selecting the category of feedback messages corresponding to the current behavior and behavior history appropriate to said user.

7. A behavior management system as in claim 1 further comprising a behavioral goal guidance and safeguards means for comparing the behavioral goal selected by the user to a stored set of goal limits, and warning the user if the selected goal exceeds an applicable goal limit.

8. A behavior management system as in claim 1 wherein the historical trend is the average caloric daily intake for a period of days.

9. A behavior management system as in claim 1 wherein the historical trend is the average weight of the user for a period of days.

10. A behavior management system as in claim 1 wherein the historical trend is the daily caloric level expended on exercise for a period of days.

11. A dietary computer comprising:
    a hand-held housing containing a processor, a display, a memory and an input which are all operatively connected;
    said memory receives and stores personal information regarding a user and behavior or dietary goals for said user, including a desired weight;

said processor generates a behavior management program by accessing said personal information, said program prompting the user regarding what foods to eat and when to eat to achieve said goals;

said display outputs recommendations generated by said processor accessing the memory, wherein said recommendations suggest what foods said user should eat;

the input receives eating behavior information indicating what foods were eaten and a weight of the user over a period of days, said processor analyzes the eating behavior information anal weight information to determine trends in the eating behavior of the user and in the weight of the user, and said processor dynamically adapts the said behavior management program in response to the trends in the eating behavior and weight of said user.

12. A dietary computer as in claim 11 wherein said behavior management program prompts said user to exercise at the time the exercise is to occur, and the display shows the exercise prompts.

13. A dietary computer as in claim 11 wherein said display shows what to eat when the predetermined meal times occur.

14. A dietary computer as in claim 11 further wherein the processor includes a behavior monitoring means for monitoring user behavior and feedback means operatively for providing feedback via the display to said user regarding compliance with said behavior management program or progress towards said behavior or dietary goals.

15. A dietary computer as in claim 14 wherein said feedback means generates feedback messages that are displayed on the display.

16. A dietary computer as in claim 15 wherein said feedback means accesses a database of feedback messages stored in the memory and indexed by a set of one or more variables, and said feedback means selects a feedback message by identification of values for said set.

17. A dietary computer as in claim 15 wherein said feedback means accesses the memory having a database of feedback messages, said feedback messages being based on both eating behavior and eating behavior history, said feedback means selecting the category of feedback messages corresponding to the current behavior and behavior history appropriate to said user.

18. A dietary computer as in claim 11, 12, 13 14, 15, 16 or 17 wherein one of said behavior or dietary goals is weight control and said memory retains information regarding the ingredients in food affecting weight control.

19. A dietary computer as in claim 11, 12, 13, 14, 15, 16 or 17 wherein one of said behaviors or dietary goals is to control cholesterol in blood and said memory retains information regarding the ingredients in food affecting cholesterol in blood.

20. A dietary computer as in claim 11, 12, 13, 14, 15, 16 or 17 wherein one of said behaviors or dietary goals is to control hypertension and said memory retains information regarding the ingredients in food affecting hypertension.

21. A dietary computer as in claim 11, 12, 13, 14, 15, 16 or 17 wherein one of said behavior or dietary goals is to control diabetes and said memory retains information regarding the ingredients in food affecting diabetes.

22. A dietary computer as in claim 11, 12, 13, 14, 15, 16 or 17 wherein said memory retains menus of meals representative of various restaurant cuisines and said display presents said menus.

23. A dietary computer as in claim 11, 12, 13, 14, 15, 16 or 17 wherein said display prominently presents the food that said user has historically selected in similar situations.

24. A self-contained behavior management apparatus comprising:

a hand-held housing;

a memory means in said housing for receiving, retaining and accessing information regarding one or more desired behaviors;

personalization means in said housing for receiving personal information regarding a user, and one or more of said user's behavior goals, and inputting said personal information into said memory means;

processing means in said housing for generating a behavior management program by accessing said memory means, said behavior program prompting the user to perform recommended behaviors, at preselected times;

behavior monitoring means in said housing for tracking user behavior, including the user's behavior and a bodily condition of the user, and for inputting data regarding said behavior and bodily condition of the user into said memory means;

analysis means for determining bodily condition trends based on the data stored in the memory means for an extended period of time;

a display operatively coupled to said processing means for presenting prompts to said user for said recommended behaviors at the preselected times, and adaptation means for adapting said behavior management program in response to both current user behavior and said bodily conditions trends, and for adjusting the prompts issued by the behavior management.

25. A behavior management apparatus as in claim 24 wherein one of said desired behaviors is eating.

26. A behavior management apparatus as in either claims 24 or 25 wherein one of said desired behaviors is exercise.

27. A portable dietary computer comprising:

a hand-held housing;

memory means in said housing for receiving and retaining information regarding a user and user behavioral goals and storing preplanned food menus;

processing means in said housing for generating a behavior management program by accessing said memory, and behavior program prompting said user to eat from selected preplanned menus at certain eating times determined by the program;

behavior monitoring means in said housing operatively coupled to a processing means for tracking the foods said user eats and for inputting data regarding said foods into said memory means and regarding a bodily condition of the user, wherein said behavior monitoring means tracks foods eaten by and the bodily condition of the user for a period of days;

output means in said housing operatively coupled to said processing means for presenting eating prompts when the certain eating times occur, and behavior adaptation means in said housing operatively coupled to said processing means for dynamically adapting said behavior program based on trends determined from in the data stored in the memory means of the foods eaten and bodily condition of the user over the period of days.

28. A dietary computer as in claim 27 further comprising a behavior feedback means operatively coupled to said processing means for generating feedback information in response to said data on eaten foods, said feedback information being displayed by said output means.

29. A dietary computer as in either claim 38 or 28 further comprising a behavioral guidance and safeguards means operatively coupled to said processing means for verifying that said behavior management program complies with guidelines stored in said memory means.

30. A self-contained behavior management system comprising:

a portable housing;

memory means in the housing for receiving, storing and accessing information regarding one or more human behaviors;

personalization means in the housing for receiving and storing in said memory means personal information on said user and the user's behavior goals;

processing means in the housing for generating a personalized behavior management program by accessing said personal information, said program prompting the user when and how to perform one or more behaviors to achieve said behavior goals, output means in the housing operatively coupled to said processing means for outputting behavior prompts to the user at times at which the behavior is scheduled by the program, behavior monitoring means for tracking the one or more behaviors performed by the user and determining trends from the behaviors over a period of days, and for tracking a condition of the user related to the goals and for determining trends in changes to the condition of the user, and an adaptation means in the housing for adapting said behavior management program in response to the trends in the one or more behaviors and in the changes to the condition of the user.

31. A behavior management system as in claim 30 further comprising a behavior monitoring means in the housing operatively coupled to said processing means for monitoring when and how one or more behaviors are performed by the user.

32. A behavior management system as in claim 30 further comprising a feedback means in the housing operatively coupled to said processing means for providing feedback messages to the user regarding user compliance to said behavior management program or user progress towards said behavior goals.

33. A behavior management system as in claim 30 wherein said output means outputs feedback messages to the user.

34. A behavior management system as in claim 30 wherein said memory means includes a database of feedback messages and said feedback means further comprises a means to index said messages using a set of one or more variables and accessing means for selecting a feedback message by identification of variable values for said set.

35. A behavior management system as in claim 33 further comprising an input receiving user behavior information and operatively coupled to said processing means, and feedback means operatively coupled to said processing means for providing feedback to the user regarding compliance with said program or progress towards said behavior goals.

36. A behavior management system as in claim 30, 31, 32, or 33 further comprising an adaptation means for adapting said behavior management program in response to said user inputs.

37. A behavior modification system as in claim 30, 31, 32, or 33 wherein said output means comprises a visual display.

38. A behavior modification system as in claim 30, 31, 32, or 33 wherein said output means comprises an audio signal generator.

* * * * *